United States Patent
Sasazawa et al.

(10) Patent No.: US 11,534,204 B2
(45) Date of Patent: Dec. 27, 2022

(54) PUNCTURE APPARATUS

(71) Applicant: TERUMO KABUSHIKI KAISHA, Tokyo (JP)

(72) Inventors: Shuhei Sasazawa, Tokyo (JP); Takeshi Akiyama, Chuo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 128 days.

(21) Appl. No.: 16/784,661

(22) Filed: Feb. 7, 2020

(65) Prior Publication Data

US 2020/0170670 A1 Jun. 4, 2020

Related U.S. Application Data

(63) Continuation of application No. PCT/JP2018/030428, filed on Aug. 16, 2018.

(30) Foreign Application Priority Data

Sep. 8, 2017 (JP) .............................. JP2017-173451

(51) Int. Cl.
*A61B 17/34* (2006.01)
*A61B 5/145* (2006.01)

(52) U.S. Cl.
CPC ...... *A61B 17/3431* (2013.01); *A61B 5/14503* (2013.01); *A61B 5/14514* (2013.01); *A61B 5/14532* (2013.01); *A61B 5/14539* (2013.01)

(58) Field of Classification Search
CPC ............ A61B 17/3431; A61B 5/14503; A61B 5/14514; A61B 5/14532; A61B 5/14539;
(Continued)

(56) References Cited

U.S. PATENT DOCUMENTS 7,758,549 B2 7/2010 Barkhahn et al.
9,937,296 B2 4/2018 Peh et al.
(Continued)

FOREIGN PATENT DOCUMENTS

EP 2 985 048 A1 2/2016
JP 2012-515016 A 7/2012
(Continued)

OTHER PUBLICATIONS

International Searching Authority, "International Search Report," issued in connection with International Patent Application No. PCT/JP2018/030428, dated Sep. 11, 2018.
(Continued)

*Primary Examiner* — Sean P Dougherty
*Assistant Examiner* — Kyle W. Kretzer
(74) *Attorney, Agent, or Firm* — Foley & Lardner LLP

(57) ABSTRACT

A puncture apparatus includes: a needle member having a tubular shape and comprising a flexible portion that is deformable; and a puncture assisting member that is movable or deformable in an axial direction of the needle member between: a restricting position in which the puncture assisting member is located outside the flexible portion of the needle member in a radial direction of the needle member, and thereby restricts deformation of the flexible portion, and a permissive position in which the puncture assisting member is not located outside the flexible portion in the radial direction, and thereby permits deformation of the flexible portion. The puncture assisting member is configured to move or deform from the restricting position to the permissive position in conjunction with an operation of inserting the flexible portion into a living body at a time of puncturing the living body with the needle member.

17 Claims, 19 Drawing Sheets

(58) Field of Classification Search
CPC .. A61M 5/158; A61M 5/3202; A61M 5/3291; A61M 25/06; A61M 5/142
See application file for complete search history.

(56) References Cited

U.S. PATENT DOCUMENTS

| | | | |
|---|---|---|---|
| 10,076,356 B2 | 9/2018 | Hadvary et al. | |
| 10,342,918 B2 | 7/2019 | Politis et al. | |
| 2007/0016149 A1* | 1/2007 | Hunn | A61M 5/158 604/272 |
| 2009/0048563 A1* | 2/2009 | Ethelfeld | A61M 5/158 604/174 |
| 2010/0249748 A1* | 9/2010 | Szucs | A61M 5/326 604/506 |
| 2013/0225997 A1 | 8/2013 | Dillard et al. | |
| 2013/0267813 A1* | 10/2013 | Pryor | A61B 5/6849 600/365 |
| 2015/0190587 A1* | 7/2015 | Peh | A61M 5/3286 604/164.08 |
| 2016/0022313 A1* | 1/2016 | Yoshida | A61B 17/3478 606/185 |
| 2016/0331358 A1* | 11/2016 | Gordon | A61B 10/04 |
| 2018/0021509 A1 | 1/2018 | Skutnik et al. | |

FOREIGN PATENT DOCUMENTS

| | | |
|---|---|---|
| JP | 2013-176559 A | 9/2013 |
| JP | 2014-510571 A | 5/2014 |
| JP | 2014-200551 A | 10/2014 |
| JP | 2015-518396 A | 7/2015 |
| JP | 2015-164545 A | 9/2015 |
| JP | 2015-529487 A | 10/2015 |
| WO | WO-2010/080715 A1 | 7/2010 |
| WO | WO-201 4/017986 A1 | 1/2014 |

OTHER PUBLICATIONS

International Searching Authority, "Written Opinion," issued in connection with International Patent Application No. PCT/JP2018/030428, dated Sep. 11, 2018.

Extended European Search Report dated Jun. 4, 2020 in corresponding European Patent Application No. 18854392.0.

* cited by examiner

[FIG. 1]
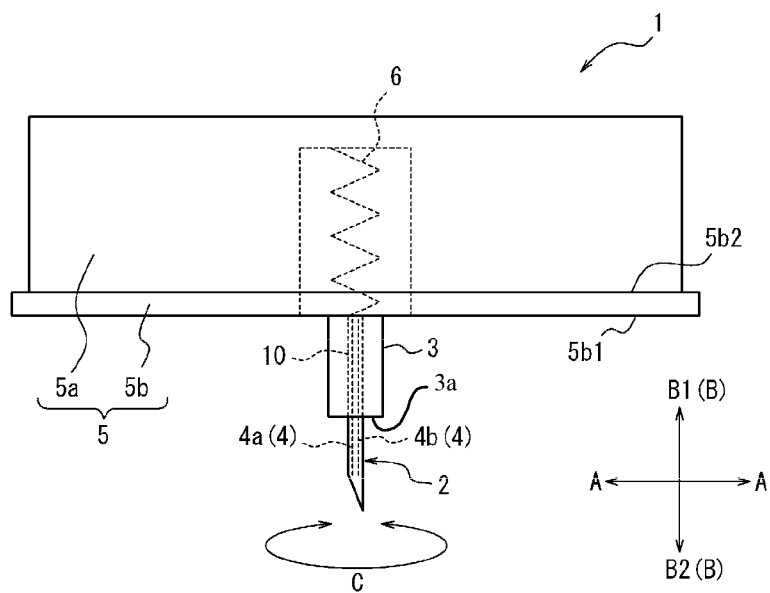
[FIG. 2]
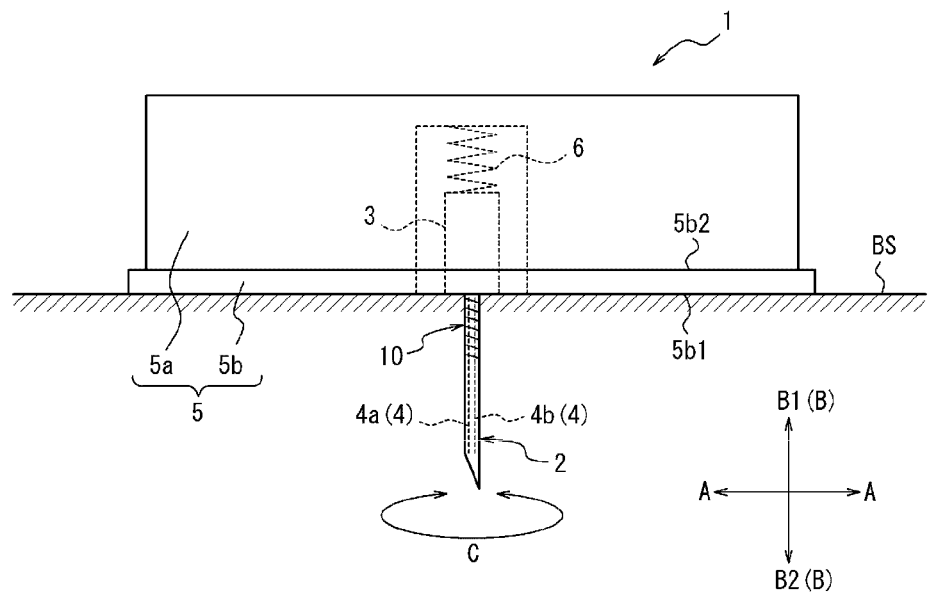

[FIG. 3]
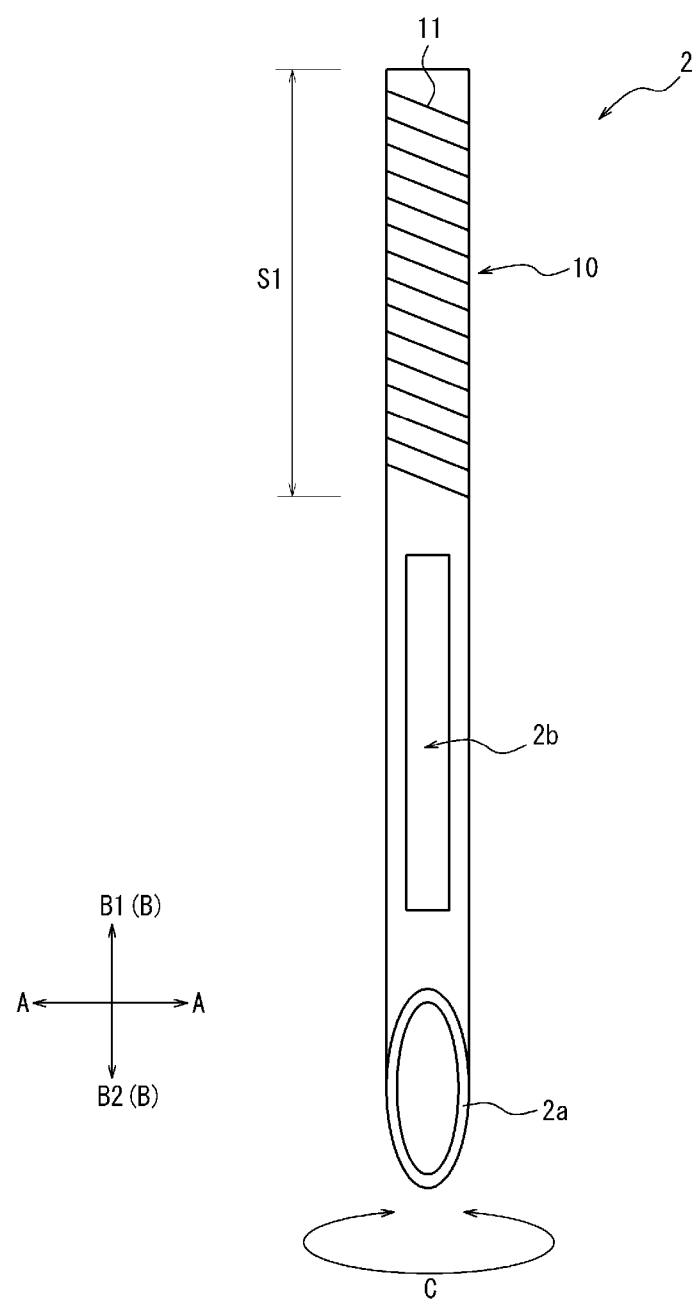

【FIG. 4 A】
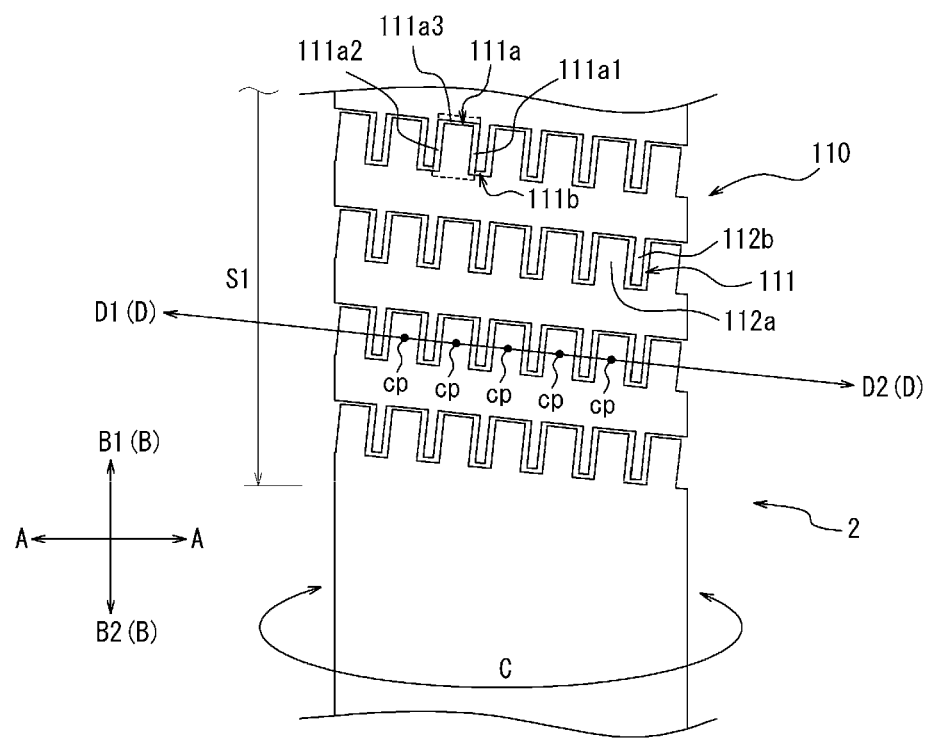
【FIG. 4 B】
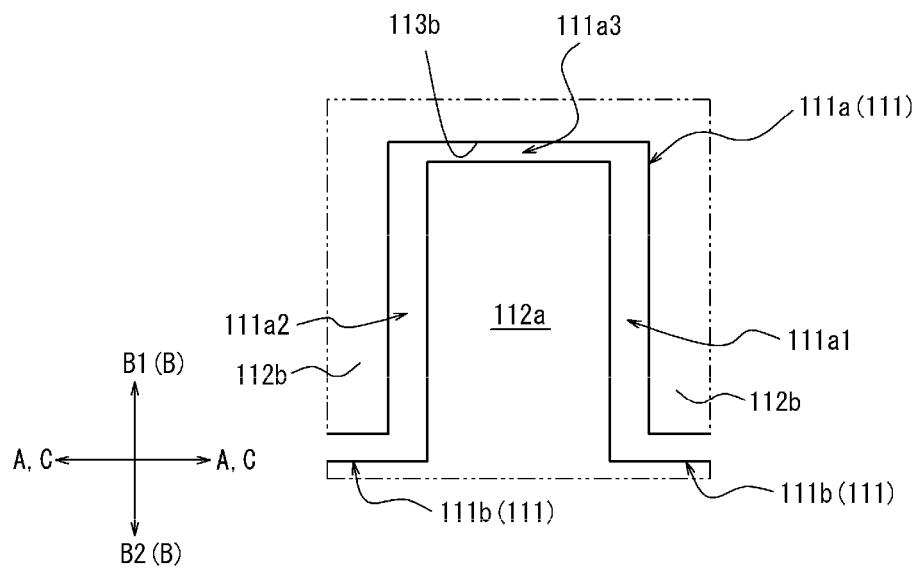

[FIG. 5 A]
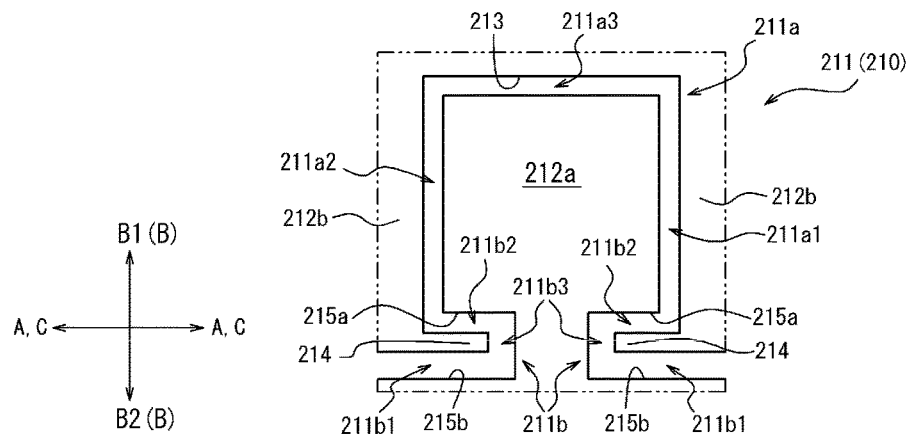
[FIG. 5 B]
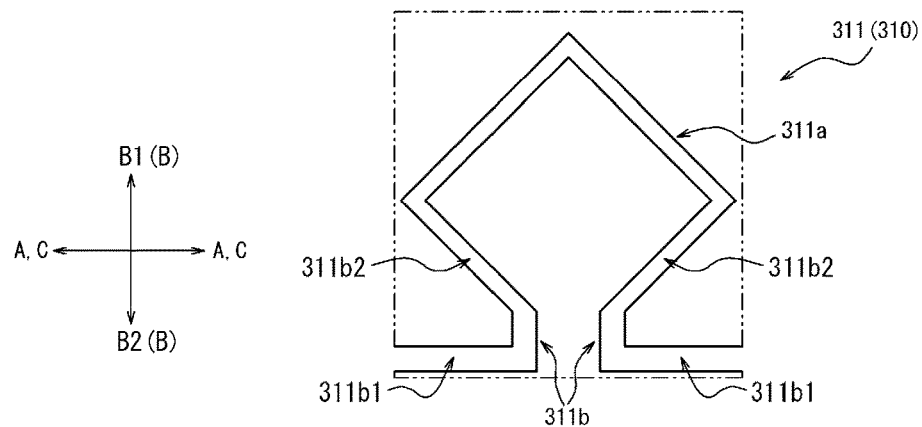
[FIG. 5 C]
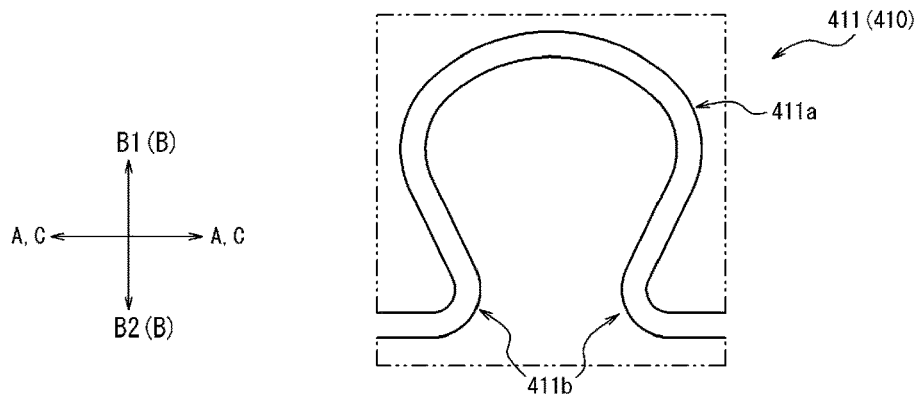

【FIG. 5 D】
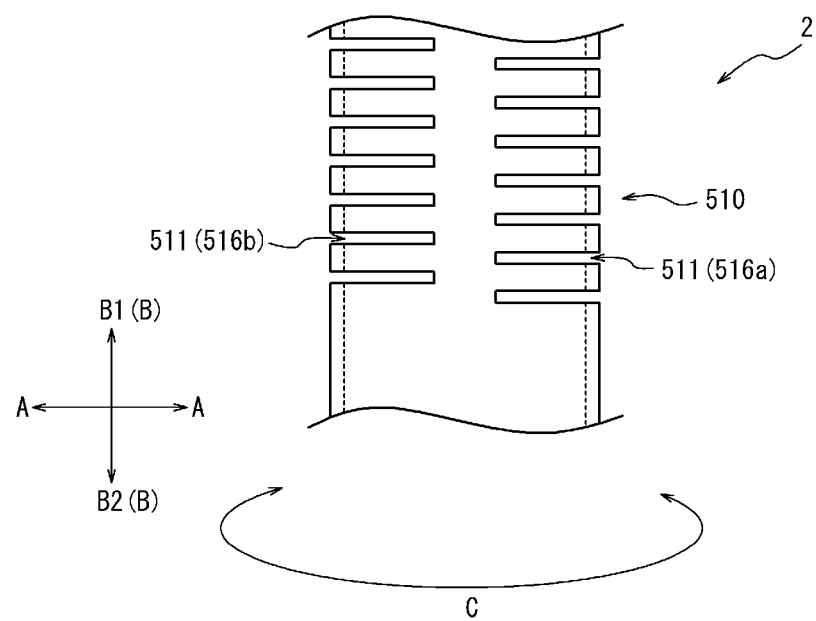

[FIG. 6]
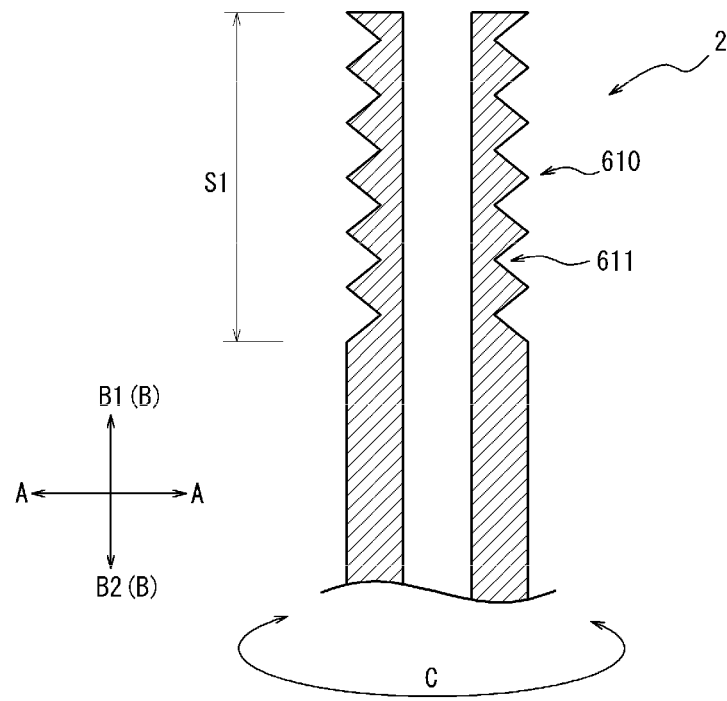
[FIG. 7]
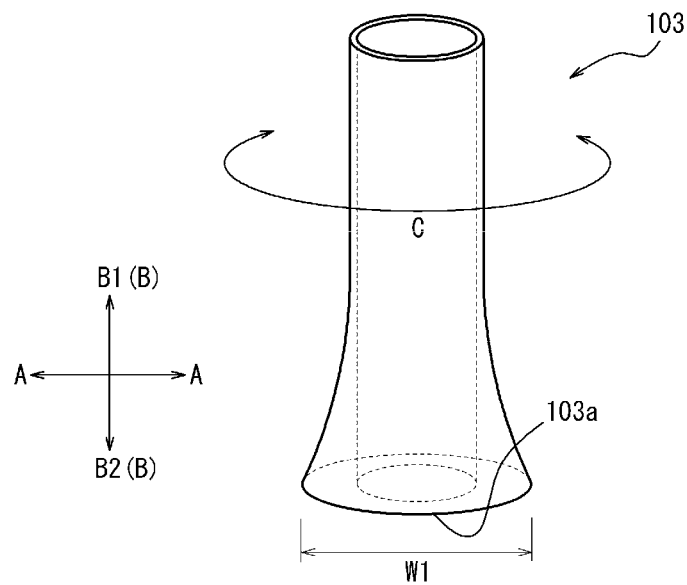

[FIG. 8 A]
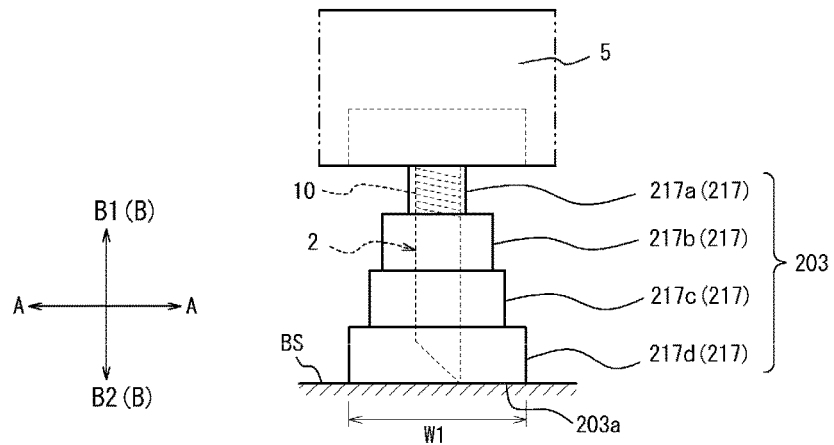
[FIG. 8 B]
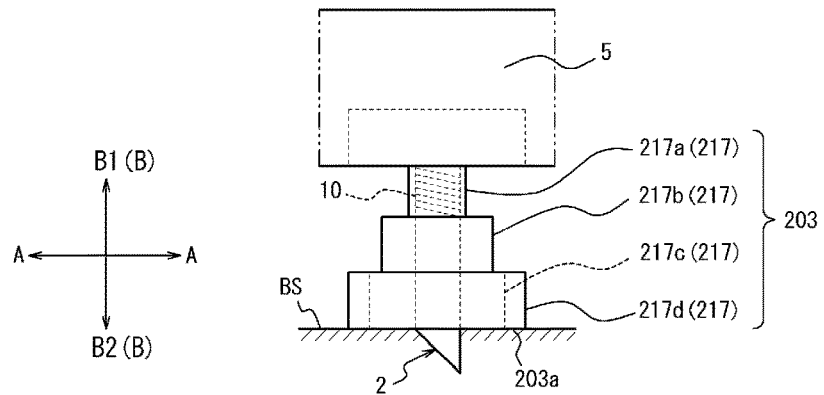
[FIG. 8 C]
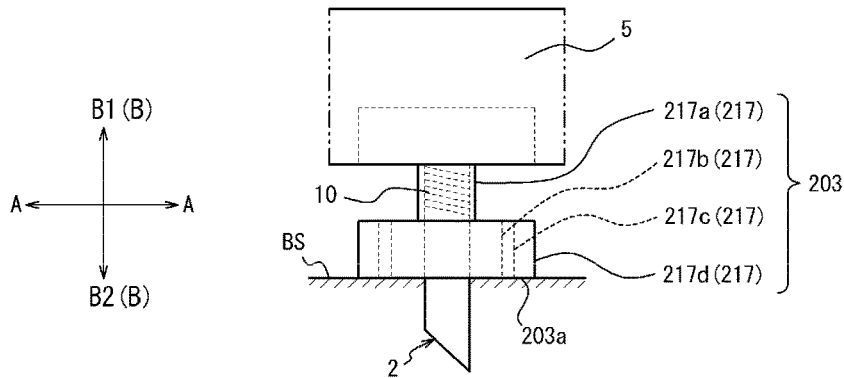

[FIG. 8 D]
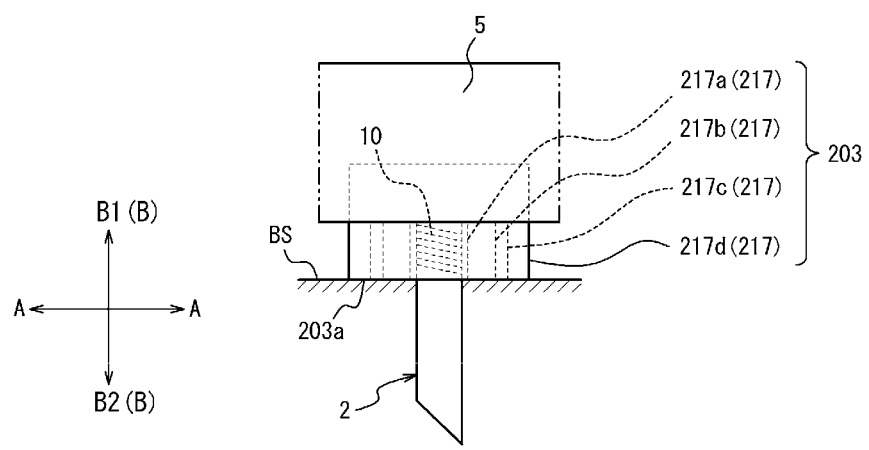
[FIG. 8 E]
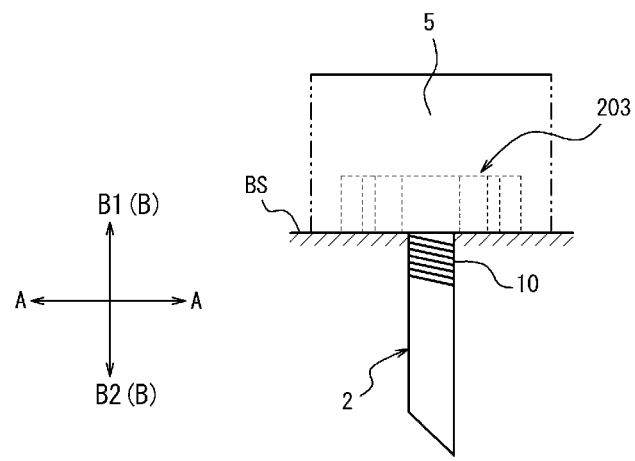

[FIG. 9]
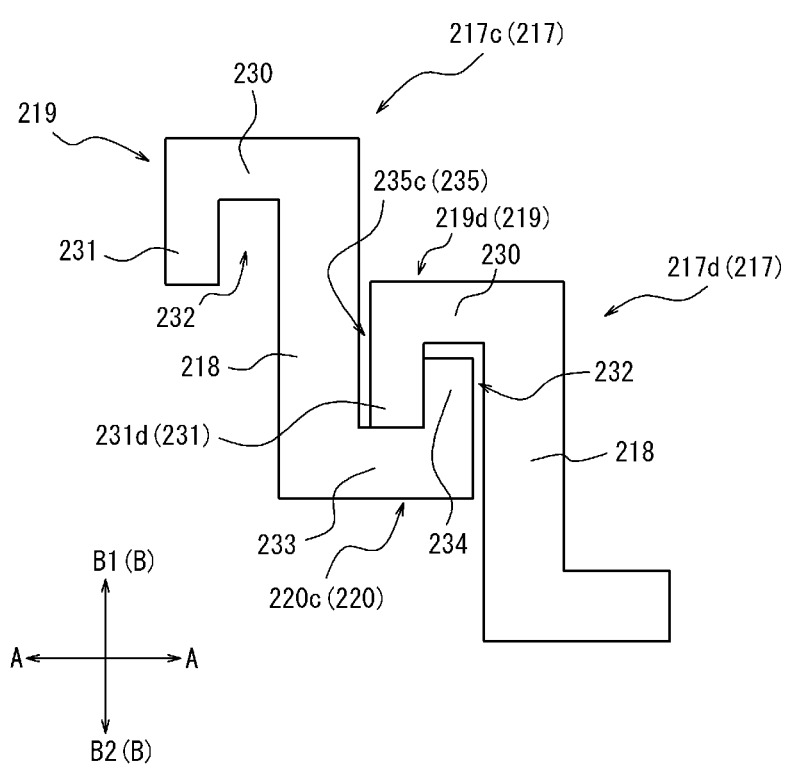

[FIG. 10A]
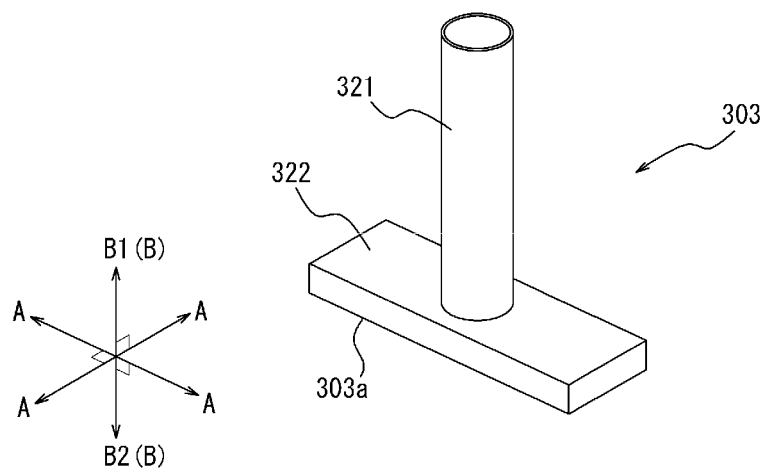
[FIG. 10B]
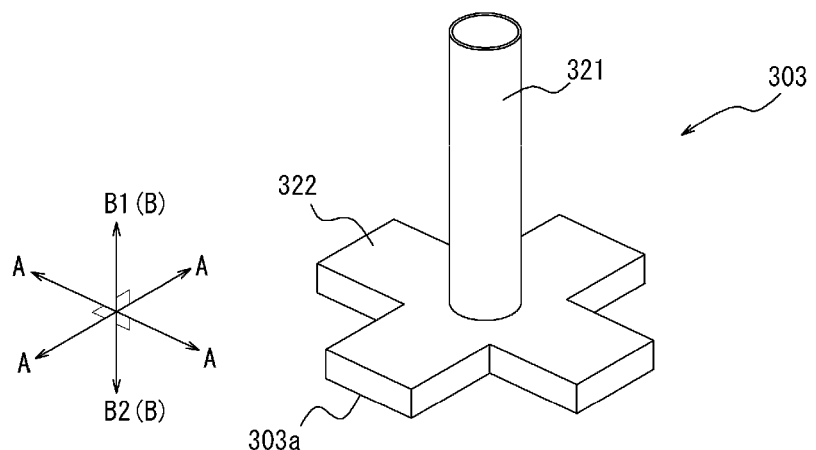

【FIG. 1 0 C】
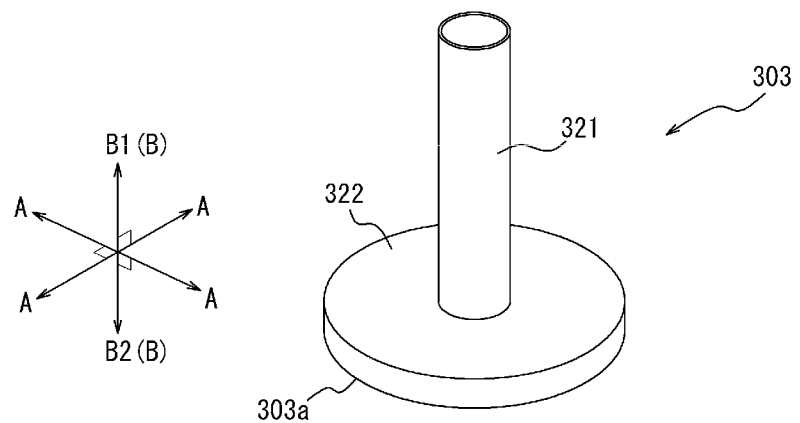

【FIG. 1 1】
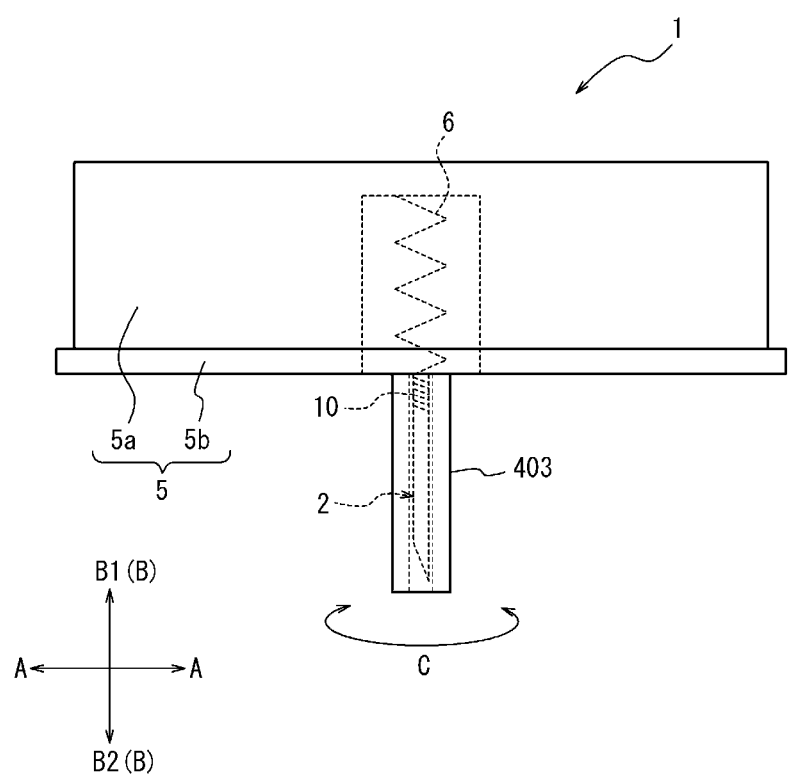

[FIG. 1 2 A]
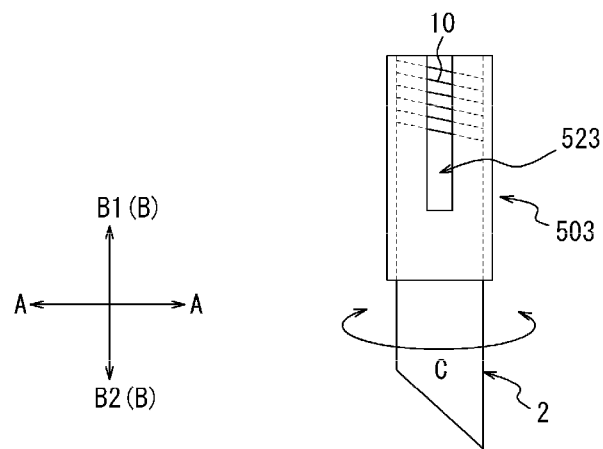
[FIG. 1 2 B]
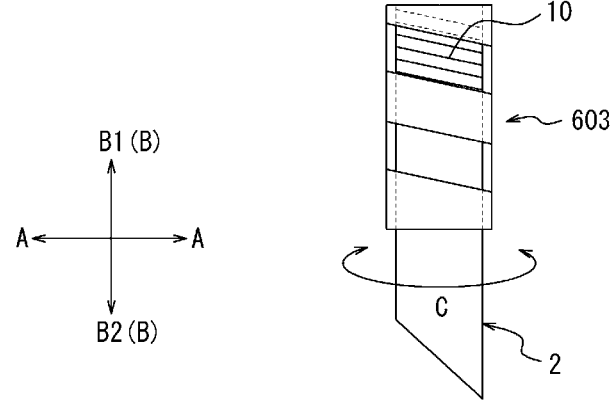

[FIG. 1 2 C]
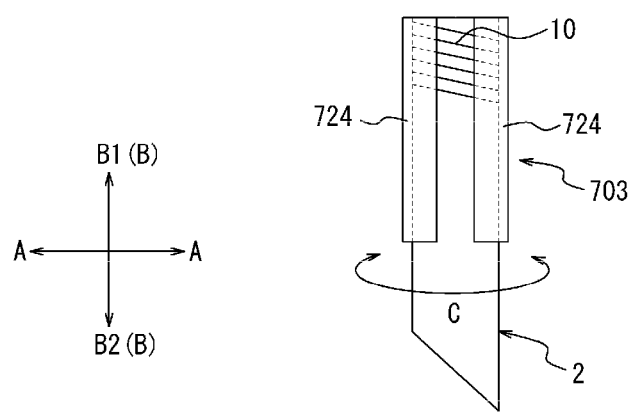

【FIG. 1 3】
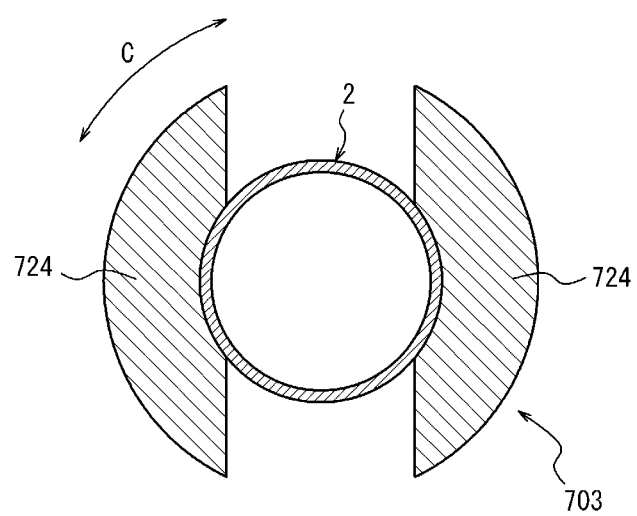

[FIG. 14]
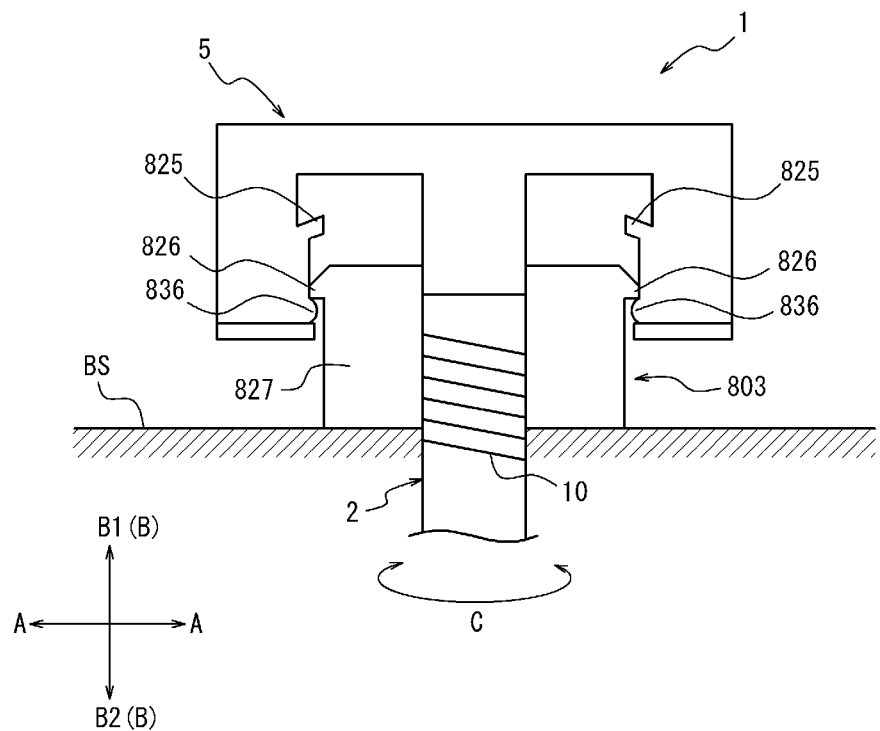
[FIG. 15]
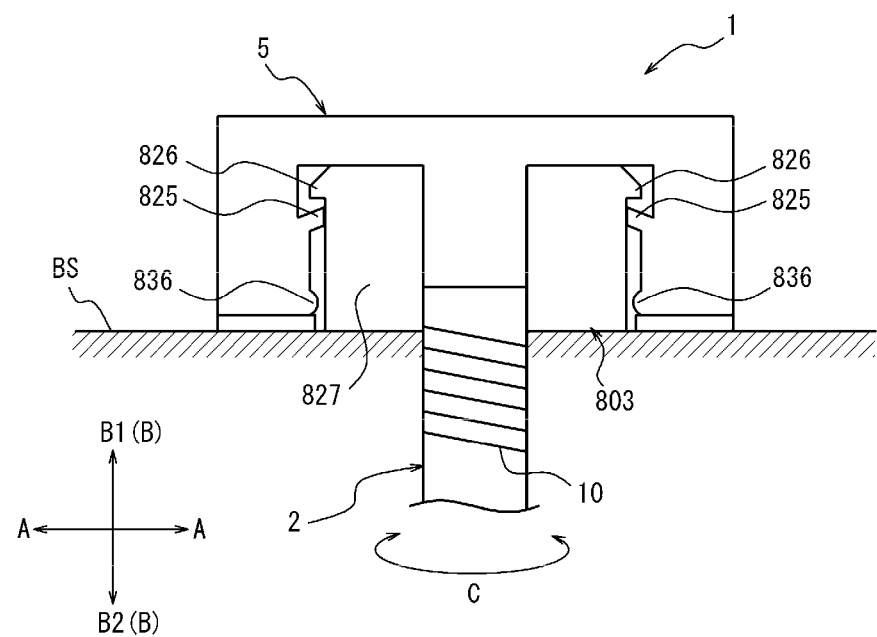

【FIG. 1 6】
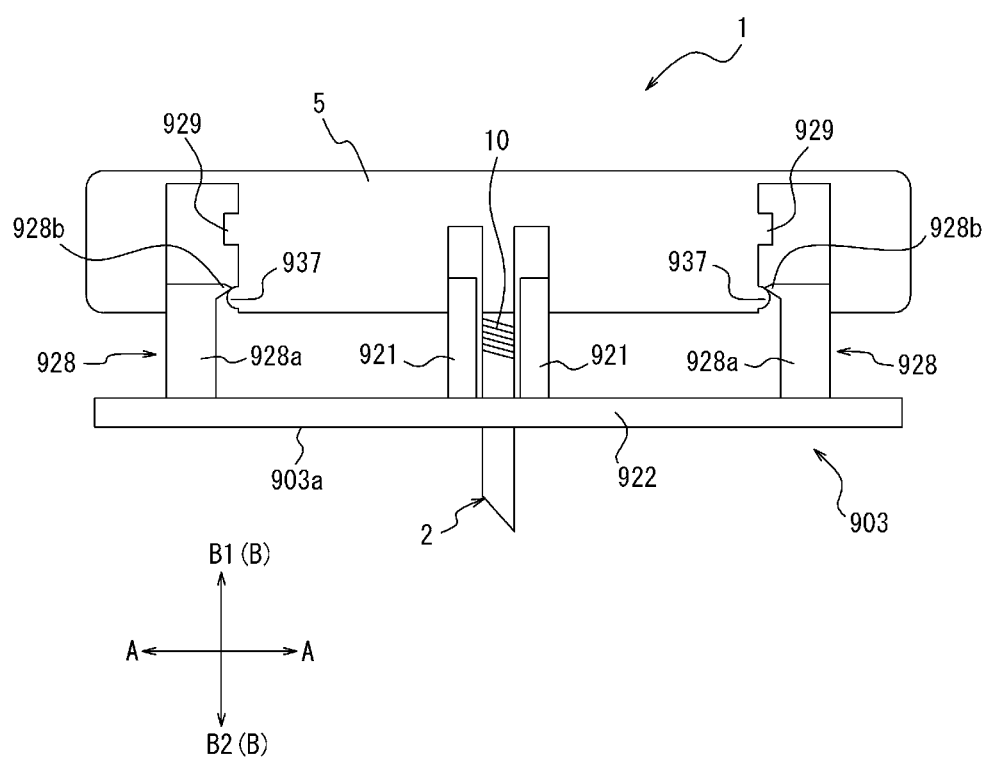

【FIG. 17A】
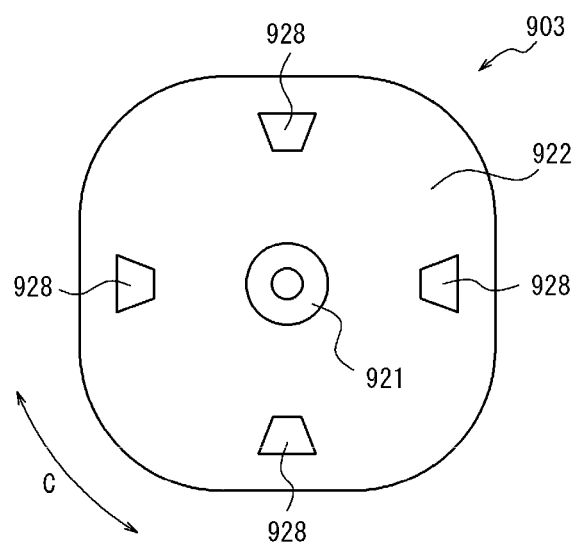
【FIG. 17B】
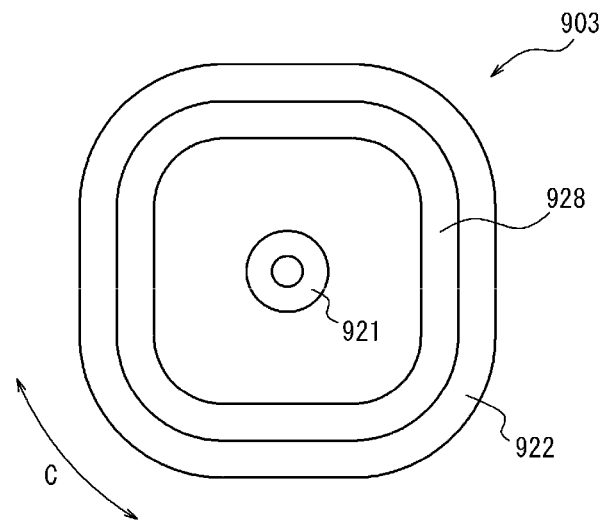

[FIG. 18]
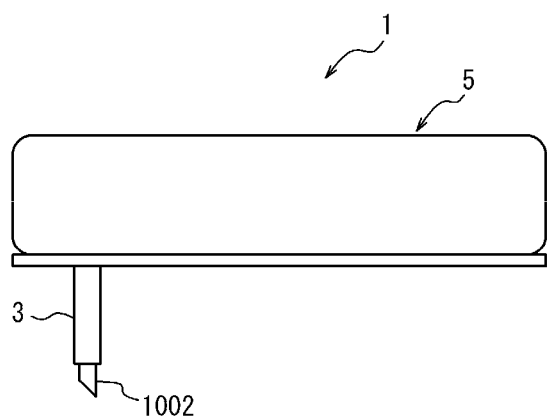
[FIG. 19]
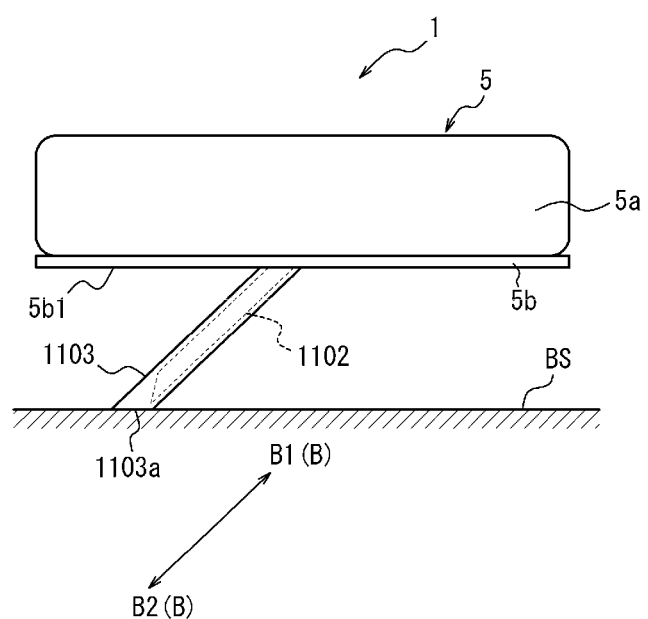

PUNCTURE APPARATUS

CROSS-REFERENCE TO RELATED APPLICATIONS

This is a bypass continuation of PCT Application No. PCT/JP2018/030428, filed on Aug. 16, 2018, which claims priority to Japanese Application No. 2017-173451, filed on Sep. 8, 2017. The contents of these applications are hereby incorporated by reference in their entireties.

BACKGROUND

The present disclosure relates to a puncture apparatus.

A needle member that is punctured through a biological surface into a living body for various purposes, such as injection of a drug solution and collection of blood, is known in the related art. For example, JP-A-2015-164545 discloses a catheter as a needle member, the catheter including a rigid main body portion and a flexible body portion.

SUMMARY

When removing a punctured needle member, a bending moment may act on the needle member. When the bending moment acts on the needle member, there is a risk of fracture of the needle member. Therefore, with the flexible body portion as in the catheter disclosed in JP-A-2015-164545, the chance that the catheter (needle member) will fracture can be inhibited.

However, in JP-A-2015-164545, a sleeve positioned outside the catheter is provided in order to allow insertion of the flexible body portion into the living body. Therefore, because the catheter and the sleeve thicker than the catheter are punctured, a person to be punctured, such as a patient, feels much more pain as compared with a case in which the patient gets punctured with only a catheter as a needle member.

Accordingly, it is an object of the present disclosure to provide a puncture apparatus having a configuration capable of reducing the chance of breakage, bending, and fracture of a needle member at the time of puncturing and removal, while alleviating the pain of a person to be punctured at the time of puncturing.

A puncture apparatus according to a first aspect of the present invention includes: a needle member having a tubular shape, the needle member including a flexible portion that is deformable; and a puncture assisting member being movable or deformable in an axial direction of the needle member between a restricting position and a permissive position, the restricting position being a position outside the flexible portion of the needle member in a radial direction of the needle member and restricting deformation of the flexible portion, the permissive position being a position not outside the flexible portion in the radial direction and permitting deformation of the flexible portion, the puncture assisting member moves or deforms from the restricting position to the permissive position in conjunction with an operation of inserting the flexible portion into the living body at the time of puncturing the living body with the needle member.

According to an embodiment of the present invention, the puncture assisting member includes an attachment section positioned at a distal end in the axial direction and configured to be attached to the biological surface when the needle member punctures the living body, and a maximum width in the radial direction of the attachment section is larger than a maximum width of the puncture assisting member in the radial direction at a position other than the attachment section.

According to an embodiment of the present invention, the puncture assisting member is cylindrical, and an outer diameter of the puncture assisting member increases from a proximal side toward the attachment section at the distal end in the axial direction.

According to an embodiment of the present invention, the cylindrical member includes a plurality of cylindrical portions concentrically overlapping one another in the radial direction, the plurality of cylindrical portions has a telescopic mechanism capable of varying a length in the axial direction by moving in the axial direction, and of outer diameters of the plurality of cylindrical portions, an outer diameter of a cylindrical portion including the attachment section is largest.

According to an embodiment of the present invention, the puncture assisting member is cylindrical, and includes a cylindrical body portion and a flange portion protruding outward in the radial direction from the cylindrical body portion at a position of the distal end of the cylindrical body portion in the axial direction, and the attachment section is formed of the flange portion.

According to an embodiment of the present invention, the puncture assisting member is cylindrical and includes a slit extending to a proximal end formed in the axial direction.

The puncture apparatus according to an embodiment of the present invention includes: a substance detector positioned in a hollow portion of the needle member and capable of detecting a substance to be measured in a living body.

The puncture apparatus according to an embodiment of the present invention includes: a processing apparatus configured to process information detected by the substance detector, and the needle member is fixed to the processing apparatus, and the puncture assisting member is attached to the processing apparatus movably or deformably in the axial direction.

According to an embodiment of the present invention, the processing apparatus includes a latch section configured to latch the puncture assisting member at the restricting position.

According to an embodiment of the present invention, the processing apparatus has a flat shape, and the needle member is fixed to one side of the processing apparatus in a thickness direction in a protruding state.

The puncture apparatus according to an embodiment of the present invention includes: a biasing member configured to bias the puncture assisting member at the permissive position in the axial direction to be restored to the restricting position.

According to an embodiment of the present invention, the flexible portion is constituted by a portion of the needle member in the axial direction where a slit extending in a spiral manner is formed.

According to an embodiment of the present invention, the slit includes a protruding slit portion protruding in the axial direction.

According to an embodiment of the present invention, if the protruding slit portion is defined as a first protruding slit portion, the slit includes a second protruding slit portion protruding in a circumferential direction of the needle member.

According to an embodiment of the present invention, the flexible portion is constituted by a portion of the needle member in the axial direction where a slit extending in a circumferential direction of the needle member is formed.

According to an embodiment of the present invention, the flexible portion is constituted by a portion of the needle member in the axial direction where a circumferential groove extending in a circumferential direction of the needle member is formed.

A puncture apparatus according to certain embodiments of the present disclosure has a configuration capable of reducing the chance of breakage, bending, and fracture of a needle member at the time of puncturing and removal, while alleviating the pain of a person to be punctured at the time of puncturing.

BRIEF DESCRIPTION OF THE DRAWINGS

FIG. 1 is a drawing illustrating a state in which a puncture assisting member is at a restricting position in a puncture apparatus according to an embodiment.

FIG. 2 is a drawing illustrating a state in which the puncture assisting member is at a permissive position in the puncture apparatus illustrated in FIG. 1.

FIG. 3 is a drawing illustrating only a needle member illustrated in FIG. 1.

FIG. 4A is a drawing illustrating a flexible portion as a modified example of the flexible portion illustrated in FIG. 3.

FIG. 4B is an enlarged view of a protruding slit portion of a slit in FIG. 4A.

FIG. 5A is a drawing illustrating another modified example of the flexible portion illustrated in FIG. 3.

FIG. 5B is a drawing illustrating another modified example of the flexible portion illustrated in FIG. 3.

FIG. 5C is a drawing illustrating another modified example of the flexible portion illustrated in FIG. 3.

FIG. 5D is a drawing illustrating another modified example of the flexible portion illustrated in FIG. 3.

FIG. 6 is a drawing illustrating another modified example of the flexible portion illustrated in FIG. 3.

FIG. 7 is a drawing illustrating only a puncture assisting member as a modified example of the puncture assisting member illustrated in FIG. 1.

FIG. 8A is a drawing illustrating a puncture assisting member as a modified example of the puncture assisting member illustrated in FIG. 1, illustrating a part of a process of deformation of the puncture assisting member when the needle member punctures a living body.

FIG. 8B is a drawing illustrating a part of the process of deformation of the puncture assisting member when the needle member punctures the living body, which is different from that of FIG. 8A.

FIG. 8C is a drawing illustrating a part of the process of deformation of the puncture assisting member when the needle member punctures the living body, which is different from FIG. 8A and FIG. 8B.

FIG. 8D is a drawing illustrating a part of the process of deformation of the puncture assisting member when the needle member punctures the living body, which is different from FIG. 8A to FIG. 8C.

FIG. 8E is a drawing illustrating a part of the process of deformation of the puncture assisting member when the needle member punctures the living body, which is different from FIG. 8A to FIG. 8D.

FIG. 9 is a drawing illustrating an inner engagement portion and an outer engagement portion.

FIG. 10A is a drawing illustrating only a puncture assisting member as a modified example of the puncture assisting member illustrated in FIG. 1.

FIG. 10B is a drawing illustrating only a puncture assisting member as a modified example of the puncture assisting member illustrated in FIG. 1.

FIG. 10C is a drawing illustrating only a puncture assisting member as a modified example of the puncture assisting member illustrated in FIG. 1.

FIG. 11 is a drawing illustrating a puncture assisting member as a modified example of the puncture assisting member illustrated in FIG. 1.

FIG. 12A is a drawing illustrating a puncture assisting member as a modified example of the puncture assisting member illustrated in FIG. 1.

FIG. 12B is a drawing illustrating a puncture assisting member as a modified example of the puncture assisting member illustrated in FIG. 1.

FIG. 12C is a drawing illustrating a puncture assisting member as a modified example of the puncture assisting member illustrated in FIG. 1.

FIG. 13 is a drawing of the needle member and the puncture assisting member illustrated in FIG. 12C as viewed in an axial direction.

FIG. 14 is a drawing illustrating a puncture assisting member as a modified example of the puncture assisting member illustrated in FIG. 1 and illustrates a state in which the puncture assisting member is at a restricting position.

FIG. 15 is a drawing illustrating a state in which the puncture assisting member illustrated in FIG. 14 is at a permissive position.

FIG. 16 is a drawing illustrating a puncture assisting member as a modified example of the puncture assisting member illustrated in FIG. 1.

FIG. 17A is a drawing illustrating an example of a latched section illustrated in FIG. 16.

FIG. 17B is a drawing illustrating an example of the latched section illustrated in FIG. 16.

FIG. 18 is a drawing illustrating a needle member and a substance detector disposed at positions different from those in FIG. 1 to FIG. 17.

FIG. 19 is a drawing illustrating the needle member and the substance detector disposed at angles different from those in FIG. 1 to FIG. 17.

DETAILED DESCRIPTION

Referring now to FIG. 1 to FIG. 19, an embodiment of a puncture apparatus will be described. The same reference numerals are given to parts and portions common to those in the respective drawings.

FIG. 1 and FIG. 2 illustrate a puncture apparatus 1 according to the present embodiment of the present invention. As illustrated in FIG. 1 and FIG. 2, the puncture apparatus 1 of the present embodiment includes a needle member 2, a puncture assisting member 3, a substance detector 4, a processing apparatus 5, and a biasing member 6. FIG. 1 illustrates a state before the needle member 2 and the substance detector 4 of the puncture apparatus 1 are inserted into a living body. FIG. 2 illustrates a state in which puncturing of the needle member 2 and the substance detector 4 of the puncture apparatus 1 into the living body is completed.

The needle member 2 is a tubular hollow needle that defines a hollow portion. The needle member 2 is provided with a deformable flexible portion 10.

Because the needle member 2 includes the flexible portion 10, when the needle member 2 punctured from a biological surface BS (see FIG. 2) into the living body is removed (hereinafter simply referred to as "at the time of removal of the needle member 2"), even if a bending moment acts on the needle member 2, the flexible portion 10 is deformed, thereby preventing the fracture of the needle member 2.

As the material of the needle member 2, for example, a metal material such as stainless steel, aluminum, an aluminum alloy, titanium, or a titanium alloy may be used.

The puncture assisting member 3 is movable or deformable in an axial direction B of the needle member 2 between a restricting position and a permissive position. The restricting position is a position outside the flexible portion 10 of the needle member 2 in a radial direction A of the needle member 2 and restricting deformation of the flexible portion 10, and the permissive position is a position not outside the flexible portion 10 in the radial direction A and permitting deformation of the flexible portion 10. Further, when puncturing the living body with the needle member 2 from the biological surface BS (see FIG. 2) (hereinafter referred to simply as "at the time of puncturing of the needle member 2"), the puncture assisting member 3 moves or deforms from the restricting position to the permissive position in conjunction with the operation of insertion of the flexible portion 10 into the living body. FIG. 1 illustrates a state in which the puncture assisting member 3 is at a restricting position, and FIG. 2 illustrates a state in which the puncture assisting member 3 is at a permissive position. Hereinafter, a direction from a distal side to a proximal side of the needle member 2 in the axial direction B of the needle member 2 is referred to as a "proximal end direction B1". In addition, a direction from the proximal side to the distal side of the needle member 2 in the axial direction B of the needle member 2 is referred to as a "distal end direction B2".

The operation and function of the puncture assisting member 3 at the time of puncturing of the needle member 2 will now be described in detail. The term "at the time of puncturing of the needle member 2" means during the operation of puncturing the living body with the needle member 2. The puncture assisting member 3 is moved or deformed from the restricting position to the permissive position in conjunction with the operation of insertion of the flexible portion 10 into the living body. In other words, as the flexible portion 10 inserts into the living body, the puncture assisting member 3 moves or deforms from the restricting position to the permissive position. In this manner, in a state in which the flexible portion 10 is still out of the living body, the puncture assisting member 3 is positioned on an outer periphery of the flexible portion 10. In other words, it corresponds to a state in which the puncture assisting member 3 is at the restricting position. Therefore, the deformation of the flexible portion 10 is restricted by the puncture assisting member 3. That is, even if a puncturing direction of the needle member 2 is deviated from the distal end direction B2 during the operation of puncturing the living body with the needle member 2, the deformation of the flexible portion 10 is restricted by the puncture assisting member 3, so that the puncturing operation can be safely performed.

Further, at the time of puncturing of the needle member 2 by the puncture assisting member 3, breakage or bending of the needle member 2 due to the deformation of the flexible portion 10 can be prevented. In contrast, when the flexible portion 10 is inserted into the living body at the time of puncturing of the needle member 2, the puncture assisting member 3 is moved or deformed from the restricting position to the permissive position. In other words, the puncture assisting member 3 is not inserted into the living body together with the flexible portion 10. In this manner, with the configuration in which the puncture assisting member 3 is not inserted into the living body, pain of a person to be punctured can be reduced when needle member 2 is inserted into the body.

As a material for the puncture assisting member 3, a resin material, for example, may be used. Examples of the resin material include: thermoplastic resins used in injection molding such as ABS resin, AS resin, polyethylene, polypropylene, polystyrene, polyvinyl chloride, polyvinylidene chloride resin, polyphenylene oxide, thermoplastic polyurethane, polymethylene methacrylate, polyoxyethylene, fluorine resin, polycarbonate, polyamide, acetal resin, acrylic resin, and polyethylene terephthalate; and thermosetting resins such as phenol resin, epoxy resin, silicone resin, and unsaturated polyester.

The substance detector 4 is positioned in the hollow portion of the needle member 2 and can detect a substance to be measured in the living body.

The substance detector 4 of the present embodiment is a linear wire member positioned in the hollow portion in the needle member 2. The substance detector 4 of the present embodiment extends along the axial direction B of the needle member 2 in the hollow portion in the needle member 2. As the substance detector 4, a member configured to detect an electric signal corresponding to an amount or concentration of the substance to be measured can be used.

More specifically, the substance detector 4 of the present embodiment is a wire electrode having a circular shape in lateral cross section. As illustrated in FIG. 1 and FIG. 2, in the present embodiment, two wire electrodes serving as the substance detector 4 are accommodated in the hollow portion of the needle member 2. The wire electrodes serving as the substance detector 4 of the present embodiment have an outer diameter of 0.02 mm to 0.2 mm. Hereinafter, when describing the two wire electrodes of the substance detector 4 without discrimination, they are correctively referred to as the "substance detector 4", and when two wire electrodes of the substance detector 4 need to be discriminated for description, one of the wire electrodes is referred to as a "first substance detector 4$a$", and the other is referred to as a "second substance detector 4$b$".

The first substance detector 4$a$ includes a detection section formed basically of a conductive core and configured to detect the substance to be measured on an outer wall of the core, and a protecting portion made of an insulating material coated on the outer wall of the core. The detection section is a working electrode configured to detect a change in electrical characteristics of the substance to be measured and is formed on the surface of the core by means of a thin film forming method such as dipping, electrolytic polymerization, sputtering, and spray coating. In the present embodiment, the second substance detector 4$b$ constitutes a reference electrode for a working electrode serving as the detection section described above. Three pieces of wire electrodes may be disposed in the hollow portion as the substance detector 4, and the three wire electrodes may constitute the working electrode, the reference electrode, and a counter electrode of the substance detectors 4, respectively. Alternatively, a configuration in which the needle member 2 itself is used as the reference electrode or the counter electrode is also applicable.

A connection section electrically connected to the processing apparatus 5 is provided at a proximal end portion of the substance detector 4 of the present embodiment. Information on the substance to be measured detected by the detection section is transmitted to the processing apparatus 5 via the connection section.

The processing apparatus 5 can process the information detected by the substance detector 4. The needle member 2 described above is fixed to the processing apparatus 5. The puncture assisting member 3 described above is attached to the processing apparatus 5 so as to be movable or deformable in the axial direction B. Specifically, the puncture assisting member 3 of the present embodiment is attached to the processing apparatus 5 so as to be movable in the axial direction B.

As illustrated in FIG. 1 and FIG. 2, the processing apparatus 5 of the present embodiment includes an apparatus main body 5a and a base plate 5b for supporting the apparatus main body 5a. In a state in which the processing apparatus 5 is indwelled on the biological surface BS, a lower surface 5b1, which is a surface on one side of the base plate 5b in a thickness direction, opposes the biological surface BS in contact, and the apparatus main body 5a is supported on an upper surface 5b2, which is a surface on the other side in the thickness direction. The apparatus main body 5a is detachably attached to the base plate 5b. In this case, the base plate 5b may support the needle member 2. An adhesive portion coated with an adhesive agent or the like is formed on the lower surface 5b1 of the base plate 5b. Puncturing of the needle member 2 of the puncture apparatus 1 of the present embodiment is completed by bringing the lower surface 5b1 of the base plate 5b into contact with the biological surface BS.

The processing apparatus 5 includes at least the apparatus main body 5a for processing information about the concentration and the amount of the substance to be measured, and for performing communication control. The processing apparatus 5 may be configured not to include the base plate 5b (see FIG. 16, which will be described later).

The processing apparatus 5 is, for example, a plate shape having a surface of approximately 30 mm×30 mm and a thickness of about 7 mm to 20 mm.

The biasing member 6 biases the puncture assisting member 3 at the permissive position in the distal end direction B2 along the axial direction B so as to restore the puncture assisting member 3 to the restricting position. By providing the biasing member 6, the puncture assisting member 3 can be returned to the initial state, that is, to the restricting position when the needle member 2 is removed. Accordingly, the puncture assisting member 3 can be reliably held at the restricting position in a state before the puncture apparatus 1 is used. As illustrated in FIG. 1 and FIG. 2, the biasing member 6 may be a coil spring positioned between the processing apparatus 5 and the puncture assisting member 3. The processing apparatus 5 is attached to the biological surface BS by a sticking portion formed of, for example, an adhesive or the like, but the biasing force of the biasing member 6 is smaller than the force applied to the biological surface BS of the sticking portion. By doing so, it is possible to prevent the sticking portion from being separated from the biological surface BS by the biasing force of the biasing member 6.

Subsequently, the puncture apparatus 1 of the present embodiment will be described further in detail.

As described above, the puncture apparatus 1 of the present embodiment includes the substance detector 4 and the processing apparatus 5 in addition to the needle member 2 and the puncture assisting member 3 and constitutes a measuring apparatus capable of measuring the substance to be measured.

A substance detector 4 accommodated in the needle member 2 detects the substance to be measured and transmits information on a detection result to the processing apparatus 5. The apparatus main body 5a of the processing apparatus 5 includes a processor, a memory, a battery, and the like, analyzes information on a detection result received from the substance detector 4, and transmits an analysis result to an external apparatus such as a display apparatus as necessary.

As illustrated in FIG. 2, the measuring apparatus as the puncture apparatus 1 of the present embodiment is attached to a person to be punctured by being in a state in which the needle member 2 and the substance detector 4 are punctured into the living body. In the state where the measuring apparatus as the puncture apparatus 1 is attached to the living body of the person to be punctured (see FIG. 2), the puncture assisting member 3 and the processing apparatus 5 are disposed on the biological surface BS of the person to be punctured. The measuring apparatus as the puncture apparatus 1 of the present embodiment measures the substance to be measured in a body fluid of the person to be punctured over time while the apparatus is attached to the person to be punctured. A time period during which the measuring apparatus as the puncture apparatus 1 of the present embodiment is attached to the person to be punctured is determined as appropriate in the judgment of the doctor or the like, for example, several hours, several days, a week, a month, and the like.

Although the substance to be measured is not particularly limited, for example, glucose, oxygen, pH, lactic acid, or the like in an interstitial fluid can be measured according to the selection of the substance detector 4.

The needle member 2 and the puncture assisting member 3 of the measuring apparatus as the puncture apparatus 1 of the present embodiment will be described in detail below.

[Needle Member 2]

FIG. 3 is a drawing illustrating only the needle member 2. As illustrated in FIG. 1 to FIG. 3, the needle member 2 of the present embodiment is a pipe body having a substantially constant outer diameter and inner diameter regardless of a position in the axial direction B. A blade surface 2a inclined with respect to the axial direction B is formed at the distal end portion in the axial direction B of the needle member 2.

However, the outer diameter and inner diameter of the needle member 2 may be gradually reduced in the distal end direction B2 along the axial direction B. Alternatively, one of the outer diameter and inner diameter of the needle member 2 may be gradually reduced in the distal end direction B2 along the axial direction B, and the other of the outer diameter and inner diameter of the needle member 2 may be substantially constant regardless of the position in the axial direction B.

A through-hole 2b is formed in a side wall of the needle member 2. The through-hole 2b is provided at a position closer to the proximal side than a region where the blade surface 2a is formed in the axial direction B, and is provided at a position closer to the distal side than a region where the flexible portion 10 is formed. By providing the through-hole 2b, a body fluid containing the substance to be measured can easily flow into the hollow portion of the needle member 2 through the through-hole 2b. Therefore, the contact between the substance to be measured and the substance detector 4 accommodated in the needle member 2 is promoted, and detection accuracy by the substance detector 4 can be enhanced.

The needle member 2 of the present embodiment is fixed to the processing apparatus 5 in a state protruding from the processing apparatus 5 on one side in the thickness direction of the processing apparatus 5 having a low-profile shape.

The flexible portion 10 of the present embodiment is provided at least on the proximal end portion of the needle member 2. More specifically, as illustrated in FIG. 3, the flexible portion 10 of the present embodiment is provided only at the proximal end portion of the needle member 2. The "proximal end of the needle member 2" means a position flush with the biological surface BS of the needle member 2 in a state in which the needle member 2 of the puncture apparatus 1 is inserted into the living body through the biological surface BS to the maximum (see FIG. 2). In the needle member 2 of the present embodiment illustrated in FIG. 2, the position of the lower surface 5b1 of the base plate 5b corresponds to the position of the proximal end of the needle member 2.

The flexible portion 10 of the present embodiment is formed preferably over a range of 1 mm or more in the distal end direction B2 along the axial direction B from the proximal end of the needle member 2 so as to be indwelled from the epidermis including at least a large number of nerves over a papillary layer and a papillary lower layer of dermis and, more preferably, formed over a range of 2 mm or more so as to be indwelled over the entire area of the dermis. Accordingly, the flexible portion 10 may be formed over the entire area (for example, 3 mm to 10 mm) from the proximal end to the distal end of the needle member 2. However, in consideration of puncture performances of the needle member 2, it is preferable to ensure a constant rigidity at the distal end portion of the needle member 2. Therefore, it is preferable that the flexible portion 10 be, for example, about one half the total length in the axial direction B of the needle member 2 from the proximal end of the needle member 2 (for example, about 1.5 mm to 5 mm). In consideration of the thickness of the dermis, the flexible portion 10 of the present embodiment is formed in a region including a proximal end portion in a range of 2 mm to 4 mm from the proximal end of the needle member 2 when the needle member 2 is completed to be inserted into the living body.

As illustrated in FIG. 3, the flexible portion 10 of the present embodiment is constituted by a portion (refer to reference numeral "S1" in FIG. 3) in which a slit 11 extending in a spiral manner along a spiral direction D in the axial direction B of the needle member 2 is formed. If the flexible portion 10 is formed by using the slit 11 extending in a spiral manner as in the present embodiment, the flexible portion 10 can be deformed in an any radial direction A. With the provision of such a flexible portion 10, the needle member 2 can be deformed in any radial direction A with respect to the processing apparatus 5. Therefore, according to the needle member 2 of the present embodiment, the flexible portion 10 can be flexibly deformed in accordance with a rotational direction of bending moment applied when the needle member 2 is removed from the inside of the living body. Therefore, it is possible to further reduce the risk of fracture when the needle member 2 is removed from the living body.

FIG. 4A is illustrates a flexible portion 110 as a modified example of the flexible portion 10 of the present embodiment illustrated in FIG. 3. In the same manner as the flexible portion 10 illustrated in FIG. 3, a flexible portion 110 illustrated in FIG. 4A is formed of a portion (see reference sign "S1" in FIG. 4A) in which a slit 111 extending in a spiral manner along the spiral direction D is formed in the axial direction B of the needle member 2. However, the slit 111 illustrated in FIG. 4A differs from the slit 11 illustrated in FIG. 3 in shape in side view when viewed from outside in the radial direction A of the needle member (see FIG. 4A).

Specifically, a plurality of protruding slit portions 111a protruding in the axial direction B are formed in the slit 111 illustrated in FIG. 4A. In the side view, positions at centers of the protruding slit portions 111a in the axial direction B and centers of the same in the circumferential direction C are defined as center points cp. The spiral direction D illustrated in FIG. 4 means an extending direction of a line formed by connecting the center points cp between the protruding slit portions 111a adjacent to each other in the circumferential direction C. Of the turning direction in the spiral direction D, the direction turning from the distal side to the proximal side of the needle member 2 is referred to as a first turning direction D1. Of the turning direction in the spiral direction D, the direction turning from the proximal side to the distal side of the needle member 2 is referred to as a second turning direction D2.

The protruding slit portions 111a each include, in sequence in the first turning direction D1 along the spiral direction D of the slit 111, a first portion 111a1 extending away from the first turning direction D1 along the spiral direction D of the slit 111 toward the proximal end direction B1 along the axial direction B, a third portion 111a3 extending toward the first turning direction D1 along the spiral direction D of the slit 111, and a second portion 111a2 extending away from the first turning direction D1 along the spiral direction D of the slit 111 in the distal end direction B2 along the axial direction B. The third portion 111a3 is a part of the slit 111 and connects the first portion 111a1 and the second portion 111a2. More specifically, although the slit 111 illustrated in FIG. 4A extends in a spiral manner, the above-described protruding slit portions 111a are formed continuously along the spiral direction D. Therefore, the slit 111 illustrated in FIG. 4A extends in a wavy shape along the spiral direction D. In this manner, by providing the protruding slit portions 111a protruding in the axial direction B in at least a part of the spiral slit 111, it is possible to prevent the flexible portion 110 from being torsionally deformed.

FIG. 4B is an enlarged view of one of the protruding slit portions 111a of the slit 111 in FIG. 4A. When the flexible portion 110 is about to be torsionally deformed, first protruding portions 112a and second protruding portions 112b butt against and interfere with each other. The first protruding portions 112a are positioned in the distal end direction B2 along the axial direction B with the protruding slit portions 111a of the slit 111 interposed therebetween. The first protruding portions 112a constitute a part of the side wall of the needle member 2, and each have a shape that is convex in the proximal end direction B1 along the axial direction B. The second protruding portions 112b are positioned in the proximal end direction B1 along the axial direction B with the protruding slit portions 111a of the slit 111 interposed therebetween. The second protruding portions 112b constitute a part of the side wall of the needle member 2, and each have a shape that is convex in the distal end direction B2 along the axial direction B. The second protruding portions 112b continue and are adjacent in the circumferential direction C of the needle member 2 to second valley bottom edge portions 113b opposing the first protruding portions 112a in the axial direction B. In other words, the first protruding portions 112a protrude in the proximal end direction B1 along the axial direction B, and the second protruding portions 112b protrude in the distal end direction B2 along the axial direction B. The first protruding portions 112a and the second protruding portions 112b are adjacent to each other in the circumferential direction C of the needle member 2 with the protruding slit portions 111a of the slit 111 interposed therebetween. The first protruding portions 112a and the second protruding portions 112b butt against and interfere with each other in the circumferential direction C, whereby the torsional deformation of the flexible portion 110 can be prevented. In the side view of the needle member 2 (see FIG. 4), an angle of the slit 111 in the spiral direction D with respect to the radial direction A of the needle member 2 is preferably in the range of 10° to 45°.

As illustrated in FIG. 4A and FIG. 4B, the plurality of protruding slit portions 111a protruding in the proximal end direction B1 along the axial direction B are alternately arranged in a spiral manner alternately with interlocking slit portions 111b. Accordingly, in other words, the plurality of first protruding portions 112a protruding from the first valley bottom edge portions 113a in the proximal end direction B1 in the axial direction B are intermittently arranged at a predetermined interval in the spiral direction D. A plurality of the second protruding portions 112b protruding from the second valley bottom edge portions 113b in the distal end direction B2 along the axial direction B are intermittently arranged at a predetermined interval in the spiral direction D. In this manner, by alternately arranging the protruding slit portions 111a and the interlocking slit portions 111b, the first protruding portions 112a and the second valley bottom edge portions 113b butt against each other in the axial direction B at the time of puncture when the largest external force in the axial direction B is applied to the needle member 2, and the second protruding portions 112b and the first valley bottom edge portions 113a butt against each other in the axial direction B. Accordingly, deformation of the flexible portion 110 in the axial direction B may be minimized. Therefore, the operation at the time of the puncturing operation can be stabilized.

FIG. 5A, FIG. 5B, and FIG. 5C are drawings illustrating another modified example of the flexible portion 10 of the present embodiment illustrated in FIG. 3. Specifically, FIG. 5A is a drawing illustrating a flexible portion 210 as a modified example of the flexible portion 10 of the present embodiment illustrated in FIG. 3. FIG. 5B is a drawing illustrating a flexible portion 310 as a modified example of the flexible portion 10 of the present embodiment illustrated in FIG. 3. FIG. 5C is a drawing illustrating a flexible portion 410 as a modified example of the flexible portion 10 of the present embodiment illustrated in FIG. 3.

Like the flexible portion 10 illustrated in FIG. 3, the flexible portion 210 illustrated in FIG. 5A is formed of a portion in which a slit 211 extending in a spiral manner is formed in the axial direction B of the needle member 2. However, the slit 211 illustrated in FIG. 5A differs from the slit 11 illustrated in FIG. 3 in shape in side view when viewed from outside in the radial direction A of the needle member 2 (see FIG. 5A). Specifically, protruding slit portions 211a protruding in the axial direction B are formed in the slit 211 illustrated in FIG. 5A. The protruding slit portions 211a each include, in sequence in the first turning direction D1 along the spiral direction D of the slit 211, a first portion 211a1 extending away from the first turning direction D1 along the spiral direction D of the slit 211 in the proximal end direction B1 along the axial direction B, a third portion 211a3 extending in the first turning direction D1 along the spiral direction D of the slit 211, and a second portion 211a2 extending away from the first turning direction D1 along the spiral direction D of the slit 211 in the distal end direction B2 along the axial direction B. The third portion 211a3 is a part of the slit 211 and connects the first portion 211a1 and the second portion 211a2. More specifically, the slit 211 illustrated in FIG. 5A extends in a spiral manner, and the above-described protruding slit portions 211a are formed continuously along the spiral direction D. Therefore, the slit 211 illustrated in FIG. 5A extends in a wavy shape along the spiral direction D. In this manner, by providing the protruding slit portions 211a protruding in the proximal end direction B1 along the axial direction B in at least a part of the spiral slit 211, it is possible to prevent the flexible portion 210 from being torsionally deformed. Specifically, when the flexible portion 210 is to be torsionally deformed, first protruding portions 212a and second protruding portions 212b butt against and interfere with each other. The first protruding portions 212a are positioned in the distal end direction B2 along the axial direction B with the protruding slit portions 211a of the slit 211 interposed therebetween. The first protruding portions 212a constitute a part of the side wall of the needle member 2, and each have a shape that is convex in the proximal end direction B1 along the axial direction B. The second protruding portions 212b are positioned in the proximal end direction B1 along the axial direction B with the protruding slit portions 211a of the slit 211 interposed therebetween. The second protruding portions 212b constitute a part of the side wall of the needle member 2, and each have a shape that is convex in the distal end direction B2 along the axial direction B. The second protruding portions 212b continue and are adjacent to valley bottom edge portions 213 opposing the first protruding portion 212a in the circumferential direction C in the axial direction B. In other words, the first protruding portions 212a protrude in the proximal end direction B1 along the axial direction B, and the second protruding portions 212b protrude in the distal end direction B2 along the axial direction B. The first protruding portions 212a and the second protruding portions 212b are adjacent to each other in the circumferential direction C of the needle member 2 with the protruding slit portions 211a of the slit 211 interposed therebetween. The first protruding portions 212a and the second protruding portions 212b butt against and interfere with each other in the circumferential direction C, whereby the torsional deformation of the flexible portion 210 can be prevented.

In addition, protruding slit portions 211b protruding in the circumferential direction C are formed in the slit 211 illustrated in FIG. 5A. Hereinafter, for convenience of description, a protruding slit portion protruding in the axial direction B will be referred to as a "first protruding slit portion", and a protruding slit portion protruding in a circumferential direction C will be referred to as a "second protruding slit portion".

The second protruding slit portions 211b of the slit 211 illustrated in FIG. 5A include, in sequence in the first turning direction D1 along the spiral direction D of the slit 211, first portions 211b1 extending toward one side in the circumferential direction C of the needle member 2, a third portion 211b3 extending from the first turning direction D1 along the spiral direction D of the slit 211 in the proximal end direction B1 along the axial direction B, and a second portion 211b2 extending away from each other toward the other side in the circumferential direction C of the needle member 2. The third portions 211b3 constitute a part of the slit 211 and connect the first portion 211b1 and the second portion 211b2. In this manner, with the provision of the second protruding slit portions 211b protruding in the circumferential direction C in at least a part of the spiral slit 211, it is possible to prevent elastic deformation of the flexible portion 210 in the axial direction B. Specifically, when the flexible portion 210 is about to be elongated and deformed in the axial direction B, interposing portions 214 butt against first opposing portions 215*a* to interfere therewith, thereby preventing elastic deformation of the flexible portion 210 in the axial direction B. Accordingly, the extension deformation of the flexible portion 210 in the axial direction B can be prevented. The interposing portions 214 are parts of a side wall of the needle member 2, and are positioned at positions interposed between the first portions 211*b*1 and the second portions 211*b*2 of the second protruding slit portions 211*b* in the axial direction B. The interposing portions 214 are parts of the second protruding portions 212*b* and are formed of portions protruding in the circumferential direction C from the distal end of the main body portion of the second protruding portions 212*b* in the distal end direction B2. The first opposing portions 215*a* are parts of a side wall of the needle member 2 and oppose each other in the axial direction B with the second portion 211*b*2 interposed therebetween on the proximal side. When the flexible portion 210 is to be compressively deformed in the axial direction B, the above-described interposing portions 214 butt against and interfered with the second opposing portions 215*b* opposed to the distal side across the first portions 211*b*1 in the axial direction B. Accordingly, the compressive deformation of the flexible portion 210 in the axial direction B may be prevented. The first opposing portions 215*a* and the second opposing portions 215*b* described above are part of the first protruding portion 212*a*.

Although the first protruding slit portion 211*a* and the second protruding slit portions 211*b* illustrated in FIG. 5A are formed continuously, these portions may be formed at separate positions apart from each other.

In addition, although the first protruding slit portion 211*a* illustrated in FIG. 5A is formed in a rectangular shape by the first portion 211*a*1, the second portion 211*a*2, and the third portion 211*a*3 extending linearly, the shape is not limited thereto, and various shapes are applicable. As illustrated in FIG. 5B, a first projection slit 311*a* may be formed in a triangular shape so as to form a vertex. Further, like a first protruding slit portion 411*a* illustrated in FIG. 5C, it may also be configured such that it extends in a curved shape.

Although the second protruding slit portions 211*b* illustrated in FIG. 5A include the first portion 211*a*1 and the second portion 211*a*2 extending substantially parallel to each other, it is not limited to this shape and may have various shapes. As in second protruding slit portions 311*b* illustrated in FIG. 5B, the first portions 311*b*1 and the second portions 311*b*2 may not be parallel to each other. Further, like second protruding slit portions 411*b* illustrated in FIG. 5C, a configuration of extending in a curved shape is also applicable.

The first protruding slit portion 311*a* and the second protruding slit portions 311*b* illustrated in FIG. 5B are formed continuously in the same manner as the first protruding slit portion 211*a* and the second protruding slit portions 211*b* illustrated in FIG. 5A, but these parts may be formed at separate positions. The same applies to the first protruding slit portion 411*a* and the second protruding slit portions 411*b* illustrated in FIG. 5C.

FIG. 5D is a drawing illustrating still another modified example of the flexible portion 10 of the present embodiment illustrated in FIG. 3. A flexible portion 510 illustrated in FIG. 5D is formed by a portion where a slit 511 extending in the circumferential direction C of the needle member 2 is formed in the axial direction B of the needle member 2. The slits 511 extend substantially in parallel to the circumferential direction C. The slits 511 are not formed over the entire area in the circumferential direction C, but are formed only in a part of the circumferential direction C. The flexible portion 510 in this configuration can be deformed in the radial direction A in the circumferential direction C at a position where the slits 511 are formed. More specifically, a plurality of the slits 511 illustrated in FIG. 5D are provided, and the plurality of slits 511 are divided into a first slit group 516*a* arranged at a predetermined interval in the axial direction B at a first predetermined position in the circumferential direction C and a second slit group 516*b* disposed at a predetermined interval in the axial direction B, at a second predetermined position in the circumferential direction C. As illustrated in FIG. 5D, the first predetermined position and the second predetermined position are opposed to each other in the radial direction A. That is, the first slit group 516*a* and the second slit group 516*b* are disposed at positions opposed to each other in the radial direction A. The flexible portion 510 illustrated in FIG. 5D is configured to be deformable only in an opposite direction (left-right direction in FIG. 5D) in which the first slit group 516*a* and the second slit group 516*b* oppose each other. In this manner, the flexible portion 510 may be deformable only in a part of the radial direction A. However, because a rotation direction of the bending moment applied to the needle member 2 at the time of removal is not constant, it is preferable to form the flexible portions 10, 110, 210, 310, and 410 that can be deformed in any direction in the radial direction A as illustrated in FIG. 3, FIG. 4A, FIG. 4B, FIG. 5A, FIG. 5B, and FIG. 5C. In particular, as illustrated in FIG. 5A, FIG. 5B, and FIG. 5C, the provision of a slit shape configured to restrict the spread of a slit gap when a force is applied to the needle member 2 in a removal direction can prevent damages caused by the needle member 2 being caught by the biological tissue when the needle member is removed from the living body.

As illustrated in FIG. 5D, the slit 511 belonging to the first slit group 516*a* and the slit 511 belonging to the second slit group 516*b* are formed at different positions in the axial direction B. In this configuration, fluctuation in strength of the flexible portion 510 in accordance with the position in the axial direction B can be reduced, and fluctuation in flexibility due to the position in the axial direction B can be reduced.

FIG. 6 is a drawing illustrating still another modified example of the flexible portion 10 of the present embodiment illustrated in FIG. 3. A flexible portion 610 illustrated in FIG. 6 is formed of a portion (see reference numeral "S1" in FIG. 6) in which a circumferential groove 611 extending in the circumferential direction C is formed in the axial direction B of the needle member 2. By forming the circumferential groove 611 and making the wall thickness thinner than the other portions, the rigidity of the portion where the circumferential groove 611 is formed can be made lower than that of the other portion. Therefore, the portion where the circumferential groove 611 is formed can be made to be the flexible portion 610 that is more easily deformed than the other portions. The depth of the circumferential groove 611 in the radial direction A is preferably, for example, 40% to 70% of the thickness of the needle member 2, and more preferably 50% to 70%. The deformability of the flexible portion 610 can be appropriately adjusted by the depth of the circumferential groove 611, the number of circumferential grooves 611, the pitch of the circumferential groove 611, and the like. In an example illustrated in FIG. 6, six circumferential grooves 611 are provided.

The rotational direction of the bending moment applied to the needle member 2 at the time of removal is not constant. Therefore, from the viewpoint of convenience of the person to be punctured, the circumferential groove 611 is preferably formed over the entire area in the circumferential direction C.

The flexible portion illustrated in FIG. 1 to FIG. 6 is preferably configured to be elastically deformable in a range smaller than 90° in a predetermined direction within the radial direction A, and more preferably, to be elastically deformable in a range of 0° to 30°. Also, the pitch in the axial direction B of the slit illustrated in FIG. 1 to FIG. 5 and the pitch in the axial direction B of the circumferential groove illustrated in FIG. 6 can be set in a range of 0.1 mm to 1.5 mm, for example, in accordance with the desired deformability of the flexible portion. If the pitch is set to be small, the deformability can be enhanced. The thickness of the needle member 2 illustrated in FIG. 1 to FIG. 6 is, for example, 25 to 33 gauges (outer diameter 0.5 mm to 0.2 mm), and its length is 3 mm to 10 mm. The thickness of the needle member 2 illustrated in FIG. 1 to FIG. 6 is set in a range of 0.02 mm to 0.15 mm, for example. In the flexible portion of the thin needle member 2, to realize the deformation performance in the range of 0° to 30° described above, the pitch in the axial direction B of the slit illustrated in FIG. 1 to FIG. 5 and the pitch in the axial direction B of the circumferential groove illustrated in FIG. 6 are preferably set in a range of 0.3 mm to 0.7 mm, and more preferably in a range of 0.4 mm to 0.6 mm.

Further, the slit illustrated in FIG. 1 to FIG. 5 and the circumferential grooves illustrated in FIG. 6 can be realized by various processing methods such as laser processing, grinding processing, and press processing, and the like.

The present embodiment illustrated in FIG. 1 to FIG. 3 will be described again with examples. As described above, the measuring apparatus as the puncture apparatus 1 of the present embodiment is maintained in a state of being attached to the person to be punctured over a period of time that is determined as appropriate in the judgment of the doctor or the like, such as several hours, several days, a week, a month, and the like. In this period, a portion of the measuring apparatus as the puncture apparatus 1 exposed outside the biological surface BS (see FIG. 2) is susceptible to an external force. When an external force is applied to the measuring apparatus as the puncture apparatus 1, the needle member 2 is pushed into the skin or subcutaneous tissue or pulled in a direction along the biological surface. At this time, the person to be punctured feels pain at a site where the needle member 2 is inserted. However, when the needle member 2 is provided with the flexible portion 10, even if an external force is applied to the measuring apparatus, the flexible portion 10 is deformed and buffered, so that damage to the skin or the subcutaneous tissue by the needle member 2 can be reduced. Therefore, the pain felt by the person to be punctured can be reduced.

When an external force equal to or greater than the fracture strength of the needle member 2 is applied to the measuring apparatus as the puncture apparatus 1 mounted on the biological surface BS, the needle member having no flexible portion 10 may fracture at a position near the biological surface BS. However, by forming the needle member 2 including the flexible portion 10, the flexible portion 10 is elastically deformed to buffer the external force, so that the needle member 2 can be prevented from fracturing. In particular, as in the present embodiment, it is preferable to provide the flexible portion 10 at least on the proximal end portion of the needle member 2. The proximal end portion of the needle member 2 is positioned in the vicinity of the biological surface BS in a state in which the measuring apparatus as the puncture apparatus 1 is attached to the living body. Therefore, it is possible to further prevent fracture of the needle member 2 in a state in which the measuring apparatus as the puncture apparatus 1 is attached to the living body.

In addition, in the present embodiment, the substance detector 4 is accommodated in the needle member 2. Therefore, in the case of a needle member without the flexible portion 10, when an external force is applied to the puncture apparatus 1 exposed outside the biological surface BS, the position in the living body tends to fluctuate, and the detection accuracy by the substance detector 4 may deteriorate. On the other hand, in the case of the needle member 2 including the flexible portion 10 of the present embodiment, even when external force is applied to the puncture apparatus 1 exposed outside the biological surface BS, the flexible portion 10 is deformed, so that the position in the living body is hardly fluctuated. As a result, it is possible to prevent a decrease in the detection accuracy by the substance detector 4.

Further, in the case of the needle member having no flexible portion 10, when a bending moment (external force in the rotational direction) acts on the needle member at the time of removal of the needle member, there is a possibility that new damage to the skin or the subcutaneous tissue is caused in addition to problems of breakage, bending and fracture of the needle member described above. In contrast, when the needle member 2 is provided with the flexible portion 10, even if an external force in the rotational direction is applied to the needle member 2 at the time of removal of the needle member 2, the flexible portion 10 is deformed, so that new damages to the skin or the subcutaneous tissue can be prevented.

[Puncture Assisting Member 3]

As illustrated in FIG. 1 and FIG. 2, the puncture assisting member 3 of the present embodiment is cylindrical, and covers the periphery of the flexible portion 10 of the needle member 2 in the radial direction A. The thickness of the puncture assisting member 3 is 1 mm to 10 mm, preferably 1 mm to 5 mm, and more preferably 2 mm to 3 mm.

The puncture assisting member 3 is provided with an attachment section 3a to be attached to the biological surface BS when puncturing the living body with the needle member 2 of the puncture apparatus 1 from the biological surface BS. The attachment section 3a of the present embodiment is formed by the distal end of the puncture assisting member 3 in the axial direction B, and butt with the biological surface BS at the time of puncturing. When the needle member 2 is further inserted into the living body from this state, the puncture assisting member 3 is pressed in the proximal end direction B1 in the axial direction B by the biological surface BS and moves in the proximal end direction B1 along the axial direction B relative to the needle member 2, and thus retracts. By the movement toward the proximal side described above, the puncture assisting member 3 moves from a position (restricting position) covering the periphery of the flexible portion 10 in the radial direction A to a position (permissive position) not covering the periphery of the flexible portion 10 in the radial direction A. In other words, the puncture assisting member 3 moves from the restricting position to the permissive position in conjunction with the puncturing operation for moving the needle member 2 in the distal end direction B2 along the axial direction B. With such a configuration, deformation of the flexible portion 10 in the radial direction A can be restricted by the puncture assisting member 3 before the flexible portion 10 is inserted into the living body. Accordingly, it is possible to prevent breakage, bending and fracture of the flexible portion 10 before being inserted into the living body. Further, the puncture assisting member 3 moves in the proximal end direction B1 along the axial direction B1 at the same time as the insertion of the flexible portion 10 into the living body. Therefore, the flexible portion 10 can be inserted into the living body without inserting the puncture assisting member 3 into the living body. Accordingly, because the needle member 2 can be punctured without puncturing the puncture assisting member 3 thicker than the needle member 2 into the living body, the pain felt by the person to be punctured can be reduced as compared with the configuration in which the puncture assisting member is punctured together.

In a state in which the puncture assisting member 3 is at the restricting position, an inner wall of the puncture assisting member 3 butts against an outer wall of the flexible portion 10, thereby restricting deformation of the flexible portion 10 in the radial direction A. In a state in which the puncture assisting member 3 is at the restricting position, a difference (clearance) between an inner diameter of the puncture assisting member 3 and an outer diameter of the flexible portion 10 of the needle member 2 is preferably 0.1 mm or less, and more preferably 0.01 mm to 0.05 mm. Within such a range, the puncture performance of the needle member 2 can be maintained while restricting the deformation of the flexible portion 10 in the radial direction A. Further, when the puncture assisting member 3 is moved from the restricting position to the permissive position, which will be described later, sliding resistance with the flexible portion 10 can be prevented from increasing, so that the operability at the time of puncturing of the needle member 2 can be enhanced.

As illustrated in FIG. 2, when the puncture assisting member 3 is moved in the proximal end direction B1 along the axial direction B with respect to the needle member 2 at the time of puncturing of the needle member 2, the puncture assisting member 3 is accommodated in the processing apparatus 5. Specifically, the puncture assisting member 3 is accommodated in the accommodation unit of the apparatus main body 5a through the opening of the base plate 5b at the time of puncturing of the needle member 2.

The puncture assisting member 3 of the present embodiment is configured to move with respect to the needle member 2 without being deformed by itself. However, a puncture assisting member configured to achieve the restricting position and the permissive position by deformation is also applicable. For example, it may also be a puncture assisting member that is formed by a bellows cylindrical member deformable in the axial direction B.

FIG. 7 is a drawing illustrating only a puncture assisting member 103 as a modified example of the puncture assisting member 3 illustrated in FIG. 1. The puncture assisting member 103 illustrated in FIG. 7 is different in shape from the puncture assisting member 3 described above. The puncture assisting member 103 illustrated in FIG. 7 is provided with an attachment section 103a to be attached to the biological surface BS (see FIG. 2) at the time of puncturing of the needle member 2. The attachment section 103a illustrated in FIG. 7 is positioned at the distal end of the puncture assisting member 103. In order to further reduce the risk that a patient as the person to be punctured touches the needle tip in use, the attachment section 103a may be provided in the distal end direction B2 along the axial direction B rather than a needle tip. As illustrated in FIG. 7, the puncture assisting member 103 is configured such that a maximum width W1 in the radial direction A of the attachment section 103a is larger than a maximum width in the radial direction A at a position other than the attachment section 103a of the puncture assisting member 103. More specifically, the puncture assisting member 103 illustrated in FIG. 7 is cylindrical, and an outer diameter of the puncture assisting member 103 increases as it goes toward the attachment section 103a in the distal end direction B2 along the axial direction B. In other words, the maximum width W1 of the attachment section 103a of the puncture assisting member 103 corresponds to the outer diameter of the attachment section 103a. With such a configuration, compared to the puncture assisting member formed to have a uniform outer diameter capable of restricting the deformation of the flexible portion 10, it is easy for an operator executing puncture to realize a state in which the entire region of the attachment section 103a in the circumferential direction C is attached to the biological surface BS (see FIG. 2) at the time of puncturing of the needle member 2. Consequently, the direction of insertion of the needle member 2 can be more stabilized.

The thickness of the puncture assisting member 103 illustrated in FIG. 7 is gradually increased in the distal end direction B2 along the axial direction B so that the inner diameter becomes constant regardless of the position in the axial direction B.

FIG. 8A, FIG. 8B, FIG. 8C, FIG. 8D, and FIG. 8E are drawings illustrating a puncture assisting member 203 as another modified example of the puncture assisting member 3 illustrated in FIG. 1. FIG. 8A to FIG. 8E illustrates a process of deformation of the puncture assisting member 203 at the time of puncturing of the needle member 2. The puncture assisting member 203 is sequentially deformed from the state illustrated in FIG. 8A to a state illustrated in FIG. 8E at the time of puncturing of the needle member 2. The puncture assisting member 203 illustrated in FIG. 8A to FIG. 8E is cylindrical similar to the puncture assisting member 3 illustrated in FIG. 1. Further, a cylindrical member as the puncture assisting member 203 includes a plurality of cylindrical portions 217 formed by concentrically overlapping in the radial direction A, and has a telescopic mechanism capable of changing the length in the axial direction B by the plurality of cylindrical portions 217 moving in the axial direction B (see FIG. 8A to FIG. 8E). The outer diameter of the cylindrical portion 217 including the attachment section 203a positioned at the distal end of the cylindrical body out of the outer diameters of the plurality of cylindrical portions 217 has a maximum outer diameter in the cylindrical member. In other words, the outer diameter of the cylindrical portion 217 including the attachment section 203a positioned at the distal end of the cylindrical member corresponds to the maximum width W1 of the attachment section 203a.

Specifically, the puncture assisting member 203 illustrated in FIG. 8 includes four cylindrical portions 217 that are concentrically overlapped with each other in the radial direction A. Each of the four cylindrical portions 217 is formed to have a uniform wall thickness. Also, the lengths of the four cylindrical portions 217 in the axial direction B are equal. More specifically, the four cylindrical portions 217 include a first cylindrical portion 217a configured to cover the periphery of the proximal end portion of the needle member 2 and having a smallest outer diameter, a second cylindrical portion 217b positioned outside the first cylindrical portion 217a in the radial direction A, a third cylindrical portion 217c positioned outside the second cylindrical portion 217b in the radial direction A, and a fourth cylindrical portion 217d positioned outside the third cylindrical portion 217c in the radial direction A and having the largest outer diameter. The attachment section 203a is formed by the distal end of the fourth cylindrical portion 217d in the axial direction B.

Each of the cylindrical portions 217 includes a cylindrical body portion 218, an inner engagement portion 219, and an outer engagement portion 220. FIG. 9 is a drawing illustrating the inner engagement portion 219 and the outer engagement portion 220. As illustrated in FIG. 9, the inner engagement portion 219 is provided to protrude toward an inner side from the cylindrical body portion 218 in the radial direction A, and is engageable with the outer engagement portion 220 of another cylindrical portion 217 adjacent thereto on the inner side in the radial direction A. Further, as illustrated in FIG. 9, the outer engagement portion 220 is provided to protrude toward an outer side from the cylindrical body portion 218 in the radial direction A, and is engageable with the inner engagement portion 219 of another cylindrical portion 217 adjacent thereto on the outer side in the radial direction A. More specifically, the inner engagement portion 219 includes an inner proximal portion 230 protruding inward in the radial direction A from the cylindrical body portion 218 and an inner distal end portion 231 extending in the distal end direction B2 along the axial direction B from an inner end of the inner proximal portion 230 in the radial direction A, and an inner concave portion 232 is formed between the cylindrical body portion 218 and the inner distal end portion 231. Further, the outer engagement portion 220 includes an outer proximal portion 233 protruding outward from the cylindrical body portion 218 in the radial direction A, and an outer distal end portion 234 extending from the outer end portion of the outer proximal portion 233 in the radial direction A in the proximal end direction B1 along the axial direction B, and an outer concave portion 235 is formed between the cylindrical body portion 218 and the outer distal end portion 234.

Focusing on the third cylindrical portion 217c and the fourth cylindrical portion 217d as an example of any two cylindrical portions 217 adjacent to each other in the radial direction A, an outer engagement portion 220c of the third cylindrical portion 217c positioned inside in the radial direction A and the inner engagement portion 219d of the fourth cylindrical portion 217d positioned outside in the radial direction A are disposed at positions overlapping each other in the axial direction B. When the fourth cylindrical portion 217d positioned outside in the radial direction A is moved in the distal side in the axial direction B with respect to the third cylindrical portion 217c positioned inside in the radial direction A, the surface (hereinafter, simply referred to as a "lower surface") of the inner engagement portion 219d of the fourth cylindrical portion 217d in the distal end direction B2 along the axial direction B butts against a surface (hereinafter simply referred to as an "upper surface") of the outer engagement portion 220c of the third cylindrical portion 217c in the proximal end direction B1 along the axial direction B, thereby restricting the further movement of the fourth cylindrical portion 217d in the distal end direction B2 along the axial direction B with respect to the third cylindrical portion 217c. At this time, the inner distal end portion 231d of the inner engagement portion 219d fits into the outer concave portion 235c of the outer engagement portion 220c.

In other words, the third cylindrical portion 217c and the fourth cylindrical portion 217d can change the total length in the axial direction B until the outer engagement portion 220c of the third cylindrical portion 217c and the inner engagement portion 219d of the fourth cylindrical portion 217d are engaged with each other (see FIG. 8 a), from a state in which these parts overlap completely with each other in the radial direction A (see FIG. 8B to FIG. 8E). Then, in a state in which the outer engagement portion 220c of the third cylindrical portion 217c engages with the inner engagement portion 219d of the fourth cylindrical portion 217d (see FIG. 8A), the inner distal end portion 231d of the inner engagement portion 219d fits into the outer concave portion 235c of the outer engagement portion 220c. At the time of puncturing of the needle member 2, the fitting state is not released unless otherwise a force greater than or equal to a predetermined value is applied to the fourth cylindrical portion 217d in the proximal end direction B1 along the axial direction B.

The engagement relationship between the third cylindrical portion 217c and the fourth cylindrical portion 217d described above is established in any two cylindrical portions 217 that are adjacent to each other in the radial direction A. Therefore, in the puncture assisting member 203 illustrated in FIG. 8A to FIG. 8E, the total length in the axial direction B can be changed to a state in which the inner engagement portion 219 and the outer engagement portion 220 of the adjacent cylindrical portions 217 are engaged (see FIG. 8A) from a state in which the four cylindrical portions 217 are completely overlapped with each other in the radial direction A (see FIG. 8D and FIG. 8E).

The flexible portion 10 illustrated in FIG. 8A to FIG. 8E is formed only at the proximal end portion of the needle member 2, and in the state illustrated in FIG. 8A and FIG. 8D, deformation in the radial direction A of the flexible portion 10 is restricted by the first cylindrical portion 217a. In other words, FIG. 8A to FIG. 8D illustrate a state in which the puncture assisting member 203 is at the restricting position. In contrast, by the movement of all the four cylindrical portions 217 in the proximal end direction B1 along the axial direction B from the state in FIG. 8D, a state illustrated in FIG. 8E in which the first cylindrical portion 217a does not cover the periphery of the flexible portion 10 is achieved. In other words, FIG. 8E illustrates a state in which the puncture assisting member 203 is at the permissive position.

FIG. 10A, FIG. 10B, and FIG. 10C are drawings illustrating only a puncture assisting member as another modified example of the puncture assisting member 3 as illustrated in FIG. 1.

The puncture assisting member 303 illustrated in FIG. 10A is cylindrical. More specifically, the puncture assisting member 303 illustrated in FIG. 10A is provided with a cylindrical body portion 321 and a flange portion 322 protruding outward in the radial direction A from the cylindrical body portion 321 at a position of the distal end in the axial direction B of the cylindrical body portion 321. The attachment section 303a to be attached to the biological surface BS (see FIG. 2) at the time of puncturing of the needle member 2 is formed of the flange portion 322. The outer shape of the flange portion 322 is not limited to the quadrangular shape illustrated in FIG. 1 OA and may be any shape. For example, a polygonal shape other than a quadrangular shape as illustrated in FIG. 10B may be used, and a circular shape or an elliptical shape as illustrated in FIG. 10C may also be used.

FIG. 11 is a drawing illustrating a puncture assisting member 403 as another modified example of the puncture assisting member 3 illustrated in FIG. 1. The puncture assisting member 403 illustrated in FIG. 11 covers not only the flexible portion 10, but also the distal end of the needle member 2 over the outer periphery thereof in the radial direction A when at the restricting position. More specifically, the puncture assisting member 403 in FIG. 11 covers not only the flexible portion 10, but also the entire needle member 2 over the outer periphery thereof in the radial direction A when at the restricting position. With the configuration in which the puncture assisting member 403 at the restricting position covers the periphery outside the distal end of the needle member 2 in the radial direction A, it is possible to prevent a person performing puncture from touching the needle tip that is the distal end of the needle member 2 before puncturing. In the case of such a configuration, it is preferable to provide the above-described biasing member 6 (see FIG. 1 and FIG. 2). In this way, the puncture assisting member 403 is restored to a position covering the periphery of the needle tip of the needle member 2 outside the radial direction A at the time of removal of the needle member 2. Therefore, even after the needle member 2 is removed, the risk that the fingertip touches the distal end of the needle member 2 can be reduced.

FIG. 12A, FIG. 12B, and FIG. 12C are drawings illustrating a puncture assisting member as another modified example of the puncture assisting member 3 as illustrated in FIG. 1. A puncture assisting member 503 illustrated in FIG. 12A is cylindrical. However, a slit 523 extending to the proximal end of the cylindrical body in the axial direction B is formed on the side wall of the cylindrical member as the puncture assisting member 503. With the provision of such a slit 523, for example, when used in conjunction with the processing apparatus 5, interference with electric wiring and a housing of the processing apparatus 5 may be avoided. The position, size and shape of the slit 523 can be appropriately designed in accordance with the position, size, shape and the like of the electric wiring and the housing of the processing apparatus 5 (see FIG. 1 and the like). Further, even when the slit 523 is used with an apparatus other than the processing apparatus 5, and even when the apparatus main body 5a is detachable, it is advantageous because it can be used to avoid interference with electric wiring, housing or the like extending from the substance detector 4.

A puncture assisting member 603 illustrated in FIG. 12B is formed by turning in a spiral manner and has a cylindrical shape as a whole. When the puncture of the needle member 2 is performed while twisting the puncture assisting member 603, the flexible portion 10 of the needle member 2 can be compressed toward the inner side in the radial direction A by the puncture assisting member 603. In other words, deformation at the position of the flexible portion 10 can be further prevented. Therefore, at the time of puncturing of the needle member 2, it is possible to further reduce the possibility of breakage, bending, or the like of the flexible portion 10.

A puncture assisting member 703 illustrated in FIG. 12C is composed of a plurality of (two in FIG. 12C) plate portions 724 disposed at different positions in the circumferential direction C. The plurality of plate portions 724 are disposed at positions outside the needle member 2 in the radial direction A, and are disposed at equal intervals in the circumferential direction C. FIG. 13 is a drawing of the needle member 2 and the puncture assisting member 703 illustrated in FIG. 12C as viewed in the axial direction B. As illustrated in FIG. 13, although the puncture assisting member 703 is formed by two plate portions 724 that are curved along the circumferential direction C, the number of plate portions and the shape thereof are not particularly limited as long as the puncture assisting member 703 at the restricting position can restrict deformation of the flexible portion 10 in the radial direction A.

FIG. 14 and FIG. 15 are drawings illustrating a puncture assisting member 803 as another modified example of the puncture assisting member 3 illustrated in FIG. 1. The puncture assisting member 803 illustrated in FIG. 14 and FIG. 15 differs from the puncture assisting member 3 illustrated in FIG. 1 in that a latched section 826 to be latched by a first latch section 825 provided in the processing apparatus 5 when accommodated in the processing apparatus 5 is provided. In other words, the processing apparatus 5 includes the first latch section 825 configured to latch the puncture assisting member 803 at the permissive position. FIG. 14 illustrates a state in which the needle member 2 is in the course of puncturing and the puncture assisting member 803 is at the restricting position. FIG. 15 illustrates a state in which puncture of the needle member 2 is completed and the puncture assisting member 803 is at the permissive position.

More specifically, the puncture assisting member 803 includes a cylindrical body portion 827 and a latched section 826 protruding to the outer side in the radial direction A from the cylindrical body portion 827. The latched section 826 may be a projection provided only in a part of the circumferential direction C or may be an annular rib provided over the entire circumferential direction C, for example. As illustrated in FIG. 14 and FIG. 15, the puncture assisting member 803 moves into the accommodation unit of the processing apparatus 5 at the time of puncturing of the needle member 2. At this time, the latched section 826 slides over the first latch section 825 formed on an inner wall of the accommodation unit of the processing apparatus 5. Therefore, even when the needle member 2 is removed, the puncture assisting member 803 is maintained in the state being latched to the processing apparatus 5 and does not return to the restricting position. The first latch section 825 may be formed of, for example, a protrusion formed on the inner wall of the accommodation unit of the processing apparatus 5.

In addition, the processing apparatus 5 illustrated in FIG. 14 and FIG. 15 includes a second latch section 836 configured to latch the puncture assisting member 803 at the restricting position. The second latch section 836 illustrated in FIG. 14 and FIG. 15 is formed by an annular rib formed on the inner wall of the accommodation unit of the processing apparatus 5. The latched section 826 and the second latch section 836 of the puncture assisting member 803 are formed at positions overlapping each other in the axial direction B. Therefore, when both the processing apparatus 5 and the puncture assisting member 803 are moved apart from each other in the axial direction B, the latched section 826 of the puncture assisting member 803 and the second latch section 836 of the processing apparatus 5 are engaged with each other. In this manner, because the processing apparatus 5 is provided with the second latch section 836, the puncture assisting member 803 at the permissive position is not separated from the processing apparatus 5. Therefore, the puncture assisting member 803 can be prevented from being unintentionally separated from the processing apparatus 5.

FIG. 16 is a drawing illustrating a puncture assisting member 903 as another modified example of the puncture assisting member 3 illustrated in FIG. 1. The puncture assisting member 903 illustrated in FIG. 16 illustrates an example in which the flange portion 322 of the puncture assisting member 303 illustrated in FIG. 10A to FIG. 10C is integrally formed with the base plate. In other words, the puncture assisting member 903 illustrated in FIG. 16 is provided with the cylindrical body portion 921 and a base plate serving as a flange portion 922 protruding outward from the cylindrical body portion 921 in the radial direction A at a position of the distal end of the cylindrical body portion 921 in the axial direction B. The attachment section 903a to be attached to the biological surface BS (see FIG. 2) at the time of puncturing of the needle member 2 is formed by the base plate serving as the flange portion 922. In other words, in the example illustrated in FIG. 16, the base plate is not part of the processing apparatus 5, but rather constitutes a part of the puncture assisting member 903. Then, the base plate as the flange portion 322 illustrated in FIG. 16 moves in the proximal end direction B1 along the axial direction B with respect to the needle member 2 at the time of puncturing of the needle member 2.

The puncture assisting member 903 illustrated in FIG. 16 includes, in addition to the cylindrical body portion 921 and the flange portion 922 described above, a latched section 928 that protrudes from the flange portion 922 toward the processing apparatus 5 at a position outside the cylindrical body portion 921 in the radial direction A. The latched section 928 is accommodated in the processing apparatus 5 when the puncture assisting member 903 is set to the permissive position from a restricting position (see FIG. 16). The latched section 928 is latched by the first latch section 929 provided on the processing apparatus 5 when being accommodated in the processing apparatus 5. In other words, the processing apparatus 5 includes a first latch section 929 configured to latch the puncture assisting member 903 at the permissive position. More specifically, the latched section 928 illustrated in FIG. 16 includes a main body portion 928a protruding from the flange portion 922 and a claw portion 928b provided on the inner side in the radial direction A of the main body portion 928a. Further, the first latch section 929 illustrated in FIG. 16 may be formed by a projection formed on the inner wall of the accommodation unit of the processing apparatus 5 for accommodating the latched section 928.

In addition, the processing apparatus 5 illustrated in FIG. 16 includes a second latch section 937 configured to latch the puncture assisting member 903 at the restricting position. The second latch section 937 illustrated in FIG. 16 is formed by an annular rib formed on the inner wall of the accommodation unit of the processing apparatus 5. The latched section 928 and the second latch section 937 of the puncture assisting member 903 are formed at positions overlapping each other in the axial direction B. Therefore, when both the processing apparatus 5 and the puncture assisting member 903 are moved apart from each other in the axial direction B, the latched section 928 of the puncture assisting member 903 and the second latch section 937 of the processing apparatus 5 are engaged with each other. In this manner, because the processing apparatus 5 is provided with the second latch section 937, the puncture assisting member 903 at the permissive position is not separated from the processing apparatus 5. Therefore, the puncture assisting member 903 can be prevented from being unintentionally separated from the processing apparatus 5.

As illustrated in FIG. 17A, a plurality of latched sections 928 may be arranged at an interval in the circumferential direction C. Further, as illustrated in FIG. 17B, an annular structure extending over the entire circumferential direction C may also be used. FIG. 17A and FIG. 17B are views of the puncture assisting member 903 as viewed from the processing apparatus 5 side (the upper side in FIG. 16).

The puncture apparatus according to the present disclosure is not limited to the specific configuration described above, and various modified examples and changes can be made without departing from the scope of the appended claims. For example, in the puncture apparatus illustrated in FIG. 1 to FIG. 17, although the needle member is protruded from a central position of the processing apparatus, the needle member is not limited thereto, and may be a needle member 1002 that protrudes from a position other than the central position of the processing apparatus 5 as illustrated in FIG. 18. In the puncture apparatus illustrated in FIG. 1 to FIG. 17, the needle member protrudes in the thickness direction of the plate-shaped processing apparatus, but is not limited to this configuration, a needle member 1102 may be inclined and protruded with respect to the thickness direction of the plate-shaped processing apparatus 5, as illustrated in FIG. 19. With such the needle member 1102, the processing apparatus 5 of the biological surface BS (see FIG. 2) can easily be moved on the biological surface BS along the axial direction B of the needle member 1102 being punctured. In other words, in the example illustrated in FIG. 19, the processing apparatus 5 can easily be moved in the left-right direction by an external force. Therefore, it is preferable that the flexible portion provided on the needle member 1102 is configured to be easily deformable in the direction along the axial direction B on the biological surface BS (in the lateral direction in FIG. 19). The distal end surface in the axial direction B constituting an attachment section 1103a of a puncture assisting member 1103 is formed at an angle substantially parallel to a lower surface 5b1 of a base plate 5b of the processing apparatus 5 so as to easily be attached with the biological surface BS at the time of the puncturing operation of the needle member 1102.

In FIG. 1 to FIG. 19, the measuring apparatus as the puncture apparatus is described, but another puncture apparatus that does not include the substance detector may also be used as another puncture apparatus. However, when a measuring apparatus including a substance detector is used as the puncture apparatus, it is possible to prevent deterioration in detection accuracy by the substance detector by providing a flexible portion as described above.

INDUSTRIAL APPLICABILITY

The present disclosure relates to a puncture apparatus.

REFERENCE SIGNS LIST

1: puncture apparatus
2, 1002, 1102: needle member
2a: blade surface
2b: through-hole
3, 103, 203, 303, 403, 503, 603, 703, 803, 903, 1103: puncture assisting member
3a, 103a, 203a, 303a, 903a, 1103a: attachment section
4: substance detector
4a: first substance detector
4b: second substance detector
5: processing apparatus
5a: apparatus main body
5b: base plate
5b1: lower surface of the base plate
5b2: upper surface of the base plate
6: biasing member
10, 110, 210, 310, 410, 510, 610: flexible portion
11, 111, 211, 311, 511: slit
111a: protruding slit portion
111a1: first portion
111a2: second portion
111a3: third portion
111b: connecting slit portion
112a, 212a: first protruding portion 112b, 212b: second protruding portion
113a: first valley bottom edge portion
113b: second valley bottom edge portion
211a: first protruding slit portion
211a1: first portion
211a2: second portion
211a3: third portion
211b: second protruding slit portion
211b1: first portion
211b2: second portion
211b3: third portion
213: valley bottom edge portion
214: interposing portion
215a: first opposing portion
215b: second opposing portion
217: cylindrical portion
217a: first cylindrical portion
217b: second cylindrical portion
217c: third cylindrical portion
217d: fourth cylindrical portion
218: cylindrical body portion
219, 219d: inner engagement portion
220, 220c: outer engagement portion
230: inner proximal portion
231, 231d: inner distal end portion
232: inner concave portion
233: outer proximal portion
234: outer distal end portion
235, 235c: outer concave portion
311a: first protruding slit portion
311a1: first portion
311a2: second portion
311b: second protruding slit portion
321: cylindrical body portion
322 flange portion
411a: first protruding slit portion
411b: second protruding slit portion
516a: first slit group
516b: second slit group
523: slit
611: circumferential groove
724: plate portion
825: first latch section
826: latched section
827: cylindrical body portion
836: second latch section
921: cylinder main body
922: flange portion
928: latched section
928a: main body portion
928b: claw portion
929: first latch section
937: second latch section
A: radial direction of needle member
B: axial direction of needle member
B1: proximal direction
B2: distal end direction
C: circumferential direction of needle member
D: spiral direction
D1: first turning direction
D2: second turning direction
cp: center point
BS: biological surface
S1: portion having slit formed in axial direction
W1: maximum width of the attachment section

The invention claimed is:

1. A puncture apparatus comprising:
a needle member having a tubular shape and comprising a flexible portion at a proximal end and a rigid portion at a distal end; and
a puncture assisting member that is movable or deformable in an axial direction of the needle member between:
a restricting position in which the puncture assisting member is in a fully extended position and extends around the flexible portion of the needle member, and thereby restricts deformation of the flexible portion, and
a permissive position in which the puncture assisting member does not extend around the flexible portion, and thereby permits deformation of the flexible portion;
wherein the puncture assisting member is configured to move or deform from the restricting position to the permissive position in conjunction with an operation of inserting the flexible portion into a living body at a time of puncturing the living body with the needle member; and
wherein, when the puncture assisting member is at the restricting position, the puncture assisting member is located at the proximal end of the needle member and the rigid portion protrudes from a distal end of the puncture assisting member.

2. The puncture apparatus according to claim 1, wherein:
the puncture assisting member comprises an attachment section positioned at a distal end of the puncture assisting member in the axial direction and configured to be attached to a biological surface of the living body, and
a maximum width of the attachment section in a radial direction is larger than a maximum width of the puncture assisting member at a position other than the attachment section in the radial direction.

3. The puncture apparatus according to claim 2, wherein:
the puncture assisting member is cylindrical, and an outer diameter of the puncture assisting member increases in the axial direction from a proximal side toward the attachment section at the distal end.

4. The puncture apparatus according to claim 2, wherein:
the puncture assisting member comprises a cylindrical body portion and a flange portion protruding outward in the radial direction from the cylindrical body portion at a position of a distal end of the cylindrical body portion in the axial direction, and
the attachment section comprises the flange portion.

5. The puncture apparatus according to claim 1, wherein:
the puncture assisting member is cylindrical and comprises a slit extending in the axial direction from a proximal end of the puncture assisting member.

6. The puncture apparatus according to claim 1, further comprising:
a substance detector positioned in a hollow portion of the needle member and configured to detect a substance to be measured in the living body.

7. The puncture apparatus according to claim 6, further comprising:
a processing apparatus configured to process information detected by the substance detector;
wherein the needle member is fixed to the processing apparatus, and the puncture assisting member is attached to the processing apparatus.

8. The puncture apparatus according to claim 7, wherein:
the processing apparatus comprises a latch section configured to latch the puncture assisting member at the restricting position.

9. The puncture apparatus according to claim 7, wherein:
the processing apparatus has a plate shape, and the needle member is fixed to the processing apparatus so as to protrude from one side of the processing apparatus in a thickness direction of the processing apparatus.

10. The puncture apparatus according to claim 1, further comprising:
a biasing member configured to bias the puncture assisting member at the permissive position in the axial direction to be restored to the restricting position.

11. The puncture apparatus according to claim 1, wherein:
the flexible portion comprises a portion of the needle member in the axial direction where a slit is formed so as to extend in a spiral manner.

12. The puncture apparatus according to claim 11, wherein:
the slit comprises a first slit portion that extends primarily in the axial direction of the needle member.

13. The puncture apparatus according to claim 12, wherein:
the slit comprises a second slit portion that extends primarily in a circumferential direction of the needle member.

14. The puncture apparatus according to claim 1, wherein:
the flexible portion comprises a portion of the needle member in the axial direction where a plurality of slits are formed so as to extend in a circumferential direction of the needle member.

15. The puncture apparatus according to claim 1, wherein:
the flexible portion comprises a portion of the needle member in the axial direction where a plurality of circumferential grooves are formed so as to extend in a circumferential direction of the needle member.

16. A method of puncturing a living body, the method comprising:
providing a puncture apparatus comprising:
a needle member having a tubular shape and comprising a flexible portion at a proximal end and a rigid portion at a distal end, and
a puncture assisting member that is movable or deformable in an axial direction of the needle member between:
a restricting position in which the puncture assisting member is in a fully extended position and extends around the flexible portion of the needle member, and thereby restricts deformation of the flexible portion,
a permissive position in which the puncture assisting member does not extend around the flexible portion, and thereby permits deformation of the flexible portion,
wherein, when the puncture assisting member is at the restricting position, the puncture assisting member is located at the proximal end of the needle member and the rigid portion protrudes from a distal end of the puncture assisting member; and
puncturing the living body with the needle member such that the flexible portion is inserted into the living body, which causes the puncture assisting member to move or deform from the restricting position to the permissive position.

17. A method of detecting a substance in a living body, the method comprising:
providing a puncture apparatus comprising:
a processing apparatus;
a needle member fixed to the processing apparatus, the needle member having a tubular shape and comprising a flexible portion at a proximal end and a rigid portion at a distal end,
a substance detector positioned in a hollow portion of the needle member, and
a puncture assisting member attached to the processing apparatus, the puncture assisting member being movable or deformable in an axial direction of the needle member between:
a restricting position in which the puncture assisting member is in a fully extended position and extends around the flexible portion of the needle member, and thereby restricts deformation of the flexible portion,
a permissive position in which the puncture assisting member does not extend around the flexible portion, and thereby permits deformation of the flexible portion,
wherein, when the puncture assisting member is at the restricting position, the puncture assisting member is located at the proximal end of the needle member and the rigid portion protrudes from a distal end of the puncture assisting member; and
puncturing the living body with the needle member such that the flexible portion is inserted into the living body, which causes the puncture assisting member to move or deform from the restricting position to the permissive position;
detecting a substance to be measured in the living body using the substance detector; and
processing information detected by the substance detector using the processing apparatus.

* * * * *